United States Patent
Pringle et al.

(10) Patent No.: US 11,037,774 B2
(45) Date of Patent: Jun. 15, 2021

(54) PHYSICALLY GUIDED RAPID EVAPORATIVE IONISATION MASS SPECTROMETRY ("REIMS")

(71) Applicant: Micromass UK Limited, Wilmslow (GB)

(72) Inventors: Steven Derek Pringle, Darwen (GB); Emrys Jones, Manchester (GB); Michael Raymond Morris, Glossop (GB); Julia Balog, Solymar (HU); James Ian Langridge, Sale (GB); Keith Richardson, High Peak (GB); Daniel Simon, Morichida (HU); Lajos Godorhazy, Erd (HU); Daniel Szalay, Budapest (HU); Zoltan Takats, Cambridge (GB)

(73) Assignee: Micromass UK Limited, Wilmslow (GB)

(*) Notice: Subject to any disclaimer, the term of this patent is extended or adjusted under 35 U.S.C. 154(b) by 566 days.

(21) Appl. No.: 15/556,052

(22) PCT Filed: Mar. 7, 2016

(86) PCT No.: PCT/GB2016/050597
§ 371 (c)(1),
(2) Date: Sep. 6, 2017

(87) PCT Pub. No.: WO2016/142669
PCT Pub. Date: Sep. 15, 2016

(65) Prior Publication Data
US 2018/0042582 A1   Feb. 15, 2018

(30) Foreign Application Priority Data

Mar. 6, 2015 (GB) ...................................... 1503863
Mar. 6, 2015 (GB) ...................................... 1503864
(Continued)

(51) Int. Cl.
H01J 49/04 (2006.01)
A61B 10/02 (2006.01)
(Continued)

(52) U.S. Cl.
CPC ............ H01J 49/049 (2013.01); A61B 1/041 (2013.01); A61B 1/2736 (2013.01);
(Continued)

(58) Field of Classification Search
CPC ............... H01J 49/0031; H01J 49/0036; H01J 49/0027; H01J 49/025; H01J 49/26;
(Continued)

(56) References Cited

U.S. PATENT DOCUMENTS 3,479,545 A  11/1969  Wilson
3,770,954 A  11/1973  Davis
(Continued)

FOREIGN PATENT DOCUMENTS

CA   2882003 A1   2/2014
CN   101170043 A  4/2008
(Continued)

OTHER PUBLICATIONS

Summons to Attend Oral Proceedings Pursuant to Rule 115(1) EPC of EP Application No. 12726643.5, dated Apr. 20, 2018, 7 pages.
(Continued)

*Primary Examiner* — Lyle Alexander
*Assistant Examiner* — Bryan Kilpatrick
(74) *Attorney, Agent, or Firm* — Kacvinsky Daisak Bluni PLLC

(57) ABSTRACT

A method is disclosed comprising obtaining physical or other non-mass spectrometric data from one or more regions of a target using a probe. The physical or other non-mass spectrometric data may be used to determine one or more regions of interest of the target. An ambient ionisation ion
(Continued)

source may then used to generate an aerosol, smoke or vapour from one or more regions of the target.

15 Claims, 9 Drawing Sheets

(30) Foreign Application Priority Data

| Mar. 6, 2015 | (GB) | 1503867 |
|---|---|---|
| Mar. 6, 2015 | (GB) | 1503876 |
| Mar. 6, 2015 | (GB) | 1503877 |
| Mar. 6, 2015 | (GB) | 1503878 |
| Mar. 6, 2015 | (GB) | 1503879 |
| Sep. 9, 2015 | (GB) | 151600 |
| Oct. 16, 2015 | (GB) | 1518369 |

(51) Int. Cl.

| A61B 17/32 | (2006.01) |
|---|---|
| A61B 18/00 | (2006.01) |
| A61B 18/14 | (2006.01) |
| A61B 18/20 | (2006.01) |
| G01N 3/00 | (2006.01) |
| G01N 9/00 | (2006.01) |
| G01N 33/68 | (2006.01) |
| H01J 49/00 | (2006.01) |
| H01J 49/06 | (2006.01) |
| H01J 49/16 | (2006.01) |
| A61B 90/13 | (2016.01) |
| A61B 1/04 | (2006.01) |
| A61B 1/273 | (2006.01) |
| A61B 5/00 | (2006.01) |
| A61B 5/01 | (2006.01) |
| A61B 5/0507 | (2021.01) |
| A61B 5/055 | (2006.01) |
| A61B 6/03 | (2006.01) |
| A61B 8/13 | (2006.01) |
| A61B 10/00 | (2006.01) |
| A61B 17/00 | (2006.01) |
| A61B 18/04 | (2006.01) |
| A61B 18/18 | (2006.01) |
| A61F 13/38 | (2006.01) |
| C12Q 1/02 | (2006.01) |
| C12Q 1/04 | (2006.01) |
| C12Q 1/18 | (2006.01) |
| C12Q 1/24 | (2006.01) |
| G01N 1/22 | (2006.01) |
| G01N 27/622 | (2021.01) |
| G01N 27/624 | (2021.01) |
| G01N 30/72 | (2006.01) |
| G01N 33/487 | (2006.01) |
| G01N 33/92 | (2006.01) |
| H01J 49/02 | (2006.01) |
| H01J 49/10 | (2006.01) |
| H01J 49/14 | (2006.01) |
| H01J 49/24 | (2006.01) |
| H01J 49/26 | (2006.01) |
| G16B 20/00 | (2019.01) |
| G16H 10/40 | (2018.01) |
| G16H 15/00 | (2018.01) |
| G16H 50/20 | (2018.01) |
| A61B 1/00 | (2006.01) |
| A61B 1/31 | (2006.01) |
| A61B 5/145 | (2006.01) |
| G06F 19/00 | (2018.01) |

(52) U.S. Cl.
CPC .......... *A61B 5/0066* (2013.01); *A61B 5/0075* (2013.01); *A61B 5/015* (2013.01); *A61B 5/055* (2013.01); *A61B 5/0507* (2013.01); *A61B 6/032* (2013.01); *A61B 6/037* (2013.01); *A61B 8/13* (2013.01); *A61B 10/00* (2013.01); *A61B 10/0041* (2013.01); *A61B 10/0233* (2013.01); *A61B 10/0283* (2013.01); *A61B 17/00* (2013.01); *A61B 17/320068* (2013.01); *A61B 18/00* (2013.01); *A61B 18/04* (2013.01); *A61B 18/042* (2013.01); *A61B 18/14* (2013.01); *A61B 18/1445* (2013.01); *A61B 18/1815* (2013.01); *A61B 18/20* (2013.01); *A61B 90/13* (2016.02); *A61F 13/38* (2013.01); *C12Q 1/025* (2013.01); *C12Q 1/04* (2013.01); *C12Q 1/18* (2013.01); *C12Q 1/24* (2013.01); *G01N 1/2202* (2013.01); *G01N 3/00* (2013.01); *G01N 9/00* (2013.01); *G01N 27/622* (2013.01); *G01N 27/624* (2013.01); *G01N 30/724* (2013.01); *G01N 33/487* (2013.01); *G01N 33/6848* (2013.01); *G01N 33/6851* (2013.01); *G01N 33/92* (2013.01); *H01J 49/0004* (2013.01); *H01J 49/0027* (2013.01); *H01J 49/0031* (2013.01); *H01J 49/0036* (2013.01); *H01J 49/025* (2013.01); *H01J 49/044* (2013.01); *H01J 49/0404* (2013.01); *H01J 49/0409* (2013.01); *H01J 49/0422* (2013.01); *H01J 49/0445* (2013.01); *H01J 49/0459* (2013.01); *H01J 49/0463* (2013.01); *H01J 49/0468* (2013.01); *H01J 49/061* (2013.01); *H01J 49/068* (2013.01); *H01J 49/10* (2013.01); *H01J 49/14* (2013.01); *H01J 49/16* (2013.01); *H01J 49/164* (2013.01); *H01J 49/24* (2013.01); *H01J 49/26* (2013.01); *A61B 1/00013* (2013.01); *A61B 1/31* (2013.01); *A61B 5/14542* (2013.01); *A61B 2010/0083* (2013.01); *A61B 2017/320069* (2017.08); *A61B 2018/00577* (2013.01); *A61B 2018/00589* (2013.01); *A61B 2018/00994* (2013.01); *A61B 2218/002* (2013.01); *A61B 2218/008* (2013.01); *G01N 33/48735* (2013.01); *G01N 2001/2223* (2013.01); *G01N 2333/195* (2013.01); *G01N 2405/00* (2013.01); *G01N 2405/04* (2013.01); *G01N 2405/08* (2013.01); *G01N 2570/00* (2013.01); *G01N 2800/26* (2013.01); *G16B 20/00* (2019.02); *G16H 10/40* (2018.01); *G16H 15/00* (2018.01); *G16H 50/20* (2018.01)

(58) Field of Classification Search
CPC ...... H01J 49/061; H01J 49/164; H01J 49/049; H01J 49/062; H01J 49/4215; H01J 49/4225; H01J 49/00; G01N 27/622; G01N 30/724; G01N 1/2202; G01N 2001/2223; G01N 30/72; A61B 2017/00022; A61B 5/00
See application file for complete search history.

(56) References Cited

U.S. PATENT DOCUMENTS

| 4,408,125 A | 10/1983 | Meuzelaar |
|---|---|---|
| H414 H | 1/1988 | Young et al. |
| 4,835,383 A | 5/1989 | Mahoney et al. |
| 4,845,367 A | 7/1989 | Amirav et al. |
| 4,883,958 A | 11/1989 | Vestal |
| 4,935,624 A | 6/1990 | Henion et al. |

(56) References Cited

U.S. PATENT DOCUMENTS

| | | |
|---|---|---|
| 5,033,541 A | 7/1991 | D'Silva |
| 5,053,343 A | 10/1991 | Vora et al. |
| 5,257,991 A | 11/1993 | Fletcher et al. |
| 5,308,977 A | 5/1994 | Oishi et al. |
| 5,374,755 A | 12/1994 | Neue et al. |
| 5,454,274 A | 10/1995 | Zhu |
| 5,509,916 A | 4/1996 | Taylor |
| 5,559,326 A | 9/1996 | Goodley et al. |
| 5,696,352 A | 12/1997 | Kourimsky |
| 5,800,597 A | 9/1998 | Perrotta et al. |
| 5,828,062 A | 10/1998 | Jarrell et al. |
| 5,830,214 A | 11/1998 | Flom et al. |
| 5,836,909 A | 11/1998 | Cosmescu |
| 5,969,352 A | 10/1999 | French et al. |
| 5,989,015 A | 11/1999 | Guerin et al. |
| 6,032,673 A | 3/2000 | Savage et al. |
| 6,333,632 B1 | 12/2001 | Yang et al. |
| 6,348,688 B1 | 2/2002 | Vestal |
| 6,825,464 B2 | 11/2004 | De La Mora |
| 6,998,622 B1 | 2/2006 | Wang et al. |
| 7,238,936 B2 | 7/2007 | Okamura et al. |
| 7,247,845 B1 | 7/2007 | Gebhardt et al. |
| 7,329,253 B2 | 2/2008 | Brounstein et al. |
| 7,335,897 B2 | 2/2008 | Takats et al. |
| 7,365,309 B2 | 4/2008 | Denny et al. |
| 7,517,348 B2 | 4/2009 | Vetter et al. |
| 7,564,028 B2 | 7/2009 | Vestal |
| 7,718,958 B2 | 5/2010 | Shiea et al. |
| 7,828,948 B1 | 11/2010 | Hatch et al. |
| 7,947,039 B2 | 5/2011 | Sartor |
| 7,960,711 B1 | 6/2011 | Sheehan et al. |
| 8,156,151 B2 | 4/2012 | Sidman |
| 8,193,487 B2 | 6/2012 | Briglin et al. |
| 8,232,520 B2 | 7/2012 | Cristoni |
| 8,253,098 B2 | 8/2012 | Hiraoka et al. |
| 8,286,260 B2 | 10/2012 | Vertes et al. |
| 8,314,382 B2 | 11/2012 | Takats |
| 8,334,504 B2 | 12/2012 | Finlay et al. |
| 8,431,409 B1 | 4/2013 | Meinhart et al. |
| 8,448,493 B2 | 5/2013 | McIntyre et al. |
| 8,481,922 B2 | 7/2013 | Musselman |
| 8,778,695 B2 | 7/2014 | Caprioli |
| 8,803,085 B2 | 8/2014 | Ouyang et al. |
| 8,834,462 B2 | 9/2014 | Johnson et al. |
| 8,970,840 B2 | 3/2015 | Kulkarni et al. |
| 9,046,448 B2 | 6/2015 | Takats |
| 9,053,914 B2 | 6/2015 | Pringle et al. |
| 9,082,603 B2 | 7/2015 | Bajic |
| 9,120,083 B2 | 9/2015 | Wyndham et al. |
| 9,255,907 B2 | 2/2016 | Heanue et al. |
| 9,281,174 B2 | 3/2016 | Takats |
| 9,287,100 B2 | 3/2016 | Szalay et al. |
| 9,709,529 B2 | 7/2017 | Takats |
| 9,731,219 B2 | 8/2017 | Wang |
| 9,947,524 B2 | 4/2018 | Pringle |
| 10,186,626 B2 | 1/2019 | Song et al. |
| 2002/0008871 A1 | 1/2002 | Poustka et al. |
| 2002/0070338 A1 | 6/2002 | Loboda |
| 2002/0076824 A1 | 6/2002 | Haglund et al. |
| 2003/0001084 A1* | 1/2003 | Bateman ............... H01J 49/004 250/281 |
| 2003/0008404 A1 | 1/2003 | Tomita et al. |
| 2003/0015657 A1 | 1/2003 | Takada et al. |
| 2003/0042412 A1 | 3/2003 | Park |
| 2003/0080278 A1 | 5/2003 | Okada et al. |
| 2003/0119193 A1 | 6/2003 | Hess et al. |
| 2003/0135222 A1 | 7/2003 | Baska |
| 2003/0136918 A1 | 7/2003 | Hartley |
| 2003/0193023 A1 | 10/2003 | Marsh |
| 2004/0007673 A1 | 1/2004 | Coon et al. |
| 2004/0079881 A1 | 4/2004 | Fischer et al. |
| 2004/0124352 A1 | 7/2004 | Kashima et al. |
| 2004/0197899 A1 | 10/2004 | Gomez et al. |
| 2004/0217274 A1 | 11/2004 | Bai et al. |
| 2004/0235395 A1 | 11/2004 | Hashish et al. |
| 2005/0017091 A1 | 1/2005 | Olsen et al. |
| 2005/0032471 A1 | 2/2005 | Pfarr et al. |
| 2005/0061779 A1 | 3/2005 | Blumenfeld et al. |
| 2005/0067565 A1 | 3/2005 | Takada et al. |
| 2005/0072916 A1 | 4/2005 | Park |
| 2005/0074361 A1 | 4/2005 | Tanoshima et al. |
| 2005/0077644 A1 | 4/2005 | Bryan et al. |
| 2005/0124986 A1 | 6/2005 | Brounstein et al. |
| 2005/0138861 A1 | 6/2005 | O'Connor |
| 2005/0154490 A1 | 7/2005 | Blaine et al. |
| 2005/0159765 A1 | 7/2005 | Moutafis et al. |
| 2005/0178962 A1 | 8/2005 | Guevremont et al. |
| 2005/0178975 A1 | 8/2005 | Glukhoy |
| 2005/0230634 A1* | 10/2005 | Bajic ..................... H01J 49/044 250/423 R |
| 2005/0230635 A1 | 10/2005 | Takats et al. |
| 2005/0258358 A1 | 11/2005 | Thakur |
| 2005/0269518 A1* | 12/2005 | Bajic ..................... H01J 49/044 250/423 F |
| 2005/0274885 A1* | 12/2005 | Brown ................. B01L 3/5088 250/288 |
| 2006/0035570 A1 | 2/2006 | Chisum et al. |
| 2006/0054806 A1 | 3/2006 | Yamada et al. |
| 2006/0091308 A1 | 5/2006 | Boyle et al. |
| 2006/0097084 A1 | 5/2006 | Gromer et al. |
| 2006/0108539 A1 | 5/2006 | Franzen |
| 2006/0113463 A1 | 6/2006 | Rossier et al. |
| 2006/0122593 A1 | 6/2006 | Jun |
| 2006/0138321 A1 | 6/2006 | Ahern et al. |
| 2006/0145089 A1 | 7/2006 | Cristoni et al. |
| 2006/0186334 A1 | 8/2006 | Jolliffe et al. |
| 2006/0250138 A1 | 11/2006 | Sparkman et al. |
| 2006/0255264 A1 | 11/2006 | Belford |
| 2007/0023631 A1 | 2/2007 | Takats et al. |
| 2007/0023677 A1 | 2/2007 | Perkins et al. |
| 2007/0094389 A1 | 4/2007 | Nussey et al. |
| 2007/0114388 A1 | 5/2007 | Ogawa et al. |
| 2007/0114394 A1 | 5/2007 | Combs et al. |
| 2007/0114437 A1 | 5/2007 | Kovtoun |
| 2007/0176113 A1 | 8/2007 | Shiea et al. |
| 2007/1081802 | 8/2007 | Yamada et al. |
| 2008/0001081 A1 | 1/2008 | Jindai et al. |
| 2008/0015278 A1 | 1/2008 | Malik et al. |
| 2008/0042056 A1 | 2/2008 | Fischer et al. |
| 2008/0067352 A1 | 3/2008 | Wang |
| 2008/0073503 A1 | 3/2008 | Wu |
| 2008/0073512 A1 | 3/2008 | Siuzdak et al. |
| 2008/0149822 A1 | 6/2008 | Vertes et al. |
| 2008/0172075 A1 | 7/2008 | Ammann |
| 2008/0173809 A1 | 7/2008 | Wu |
| 2008/0234579 A1 | 9/2008 | Halevy-Politch et al. |
| 2008/0312651 A1 | 12/2008 | Pope et al. |
| 2009/0065714 A1 | 3/2009 | Keady |
| 2009/0082637 A1 | 3/2009 | Galperin |
| 2009/0126891 A1 | 5/2009 | Koivunen et al. |
| 2009/0159790 A1 | 6/2009 | Kostiainen et al. |
| 2009/0272893 A1 | 11/2009 | Hieftje et al. |
| 2009/0302211 A1 | 12/2009 | Takats |
| 2010/0012830 A1 | 1/2010 | Cristoni |
| 2010/0072359 A1 | 3/2010 | Briglin et al. |
| 2010/0078550 A1 | 4/2010 | Wiseman et al. |
| 2010/0101304 A1 | 4/2010 | McIntyre et al. |
| 2010/0176290 A1 | 7/2010 | Vidal-de-Miguel |
| 2010/0186524 A1 | 7/2010 | Ariessohn et al. |
| 2010/0229263 A1 | 9/2010 | Vertes et al. |
| 2011/0036978 A1 | 2/2011 | Franzen |
| 2011/0049352 A1 | 3/2011 | Ding et al. |
| 2011/0059554 A1 | 3/2011 | Albers et al. |
| 2011/0066147 A1 | 3/2011 | He et al. |
| 2011/0087308 A1 | 4/2011 | Morgan et al. |
| 2011/0121173 A1 | 5/2011 | Koenig et al. |
| 2011/0295250 A1 | 12/2011 | Johnson et al. |
| 2012/0018628 A1 | 1/2012 | Wuijckhuijse et al. |
| 2012/0043460 A1 | 2/2012 | Wouters et al. |
| 2012/0048264 A1 | 3/2012 | Finlay et al. |
| 2012/0074306 A1 | 3/2012 | Jesse et al. |
| 2012/0079894 A1 | 4/2012 | Berkel et al. |
| 2012/0080592 A1 | 4/2012 | Wiseman et al. |
| 2012/0085649 A1 | 4/2012 | Sane et al. |

(56) References Cited

U.S. PATENT DOCUMENTS

| | | | |
|---|---|---|---|
| 2012/0119079 | A1 | 5/2012 | Ouyang et al. |
| 2012/0149009 | A1 | 6/2012 | Levis et al. |
| 2012/0156712 | A1 | 6/2012 | Takats |
| 2012/0295276 | A1 | 11/2012 | Cooks et al. |
| 2013/0123919 | A1 | 5/2013 | Goldstein et al. |
| 2013/0178845 | A1 | 7/2013 | Smith et al. |
| 2013/0181126 | A1 | 7/2013 | Jong |
| 2013/0303846 | A1 | 11/2013 | Cybulski et al. |
| 2014/0151547 | A1 | 6/2014 | Bajic |
| 2014/0268134 | A1 | 9/2014 | O'Connor |
| 2014/0276775 | A1 | 9/2014 | Funk et al. |
| 2014/0291506 | A1 | 10/2014 | Tikhonski et al. |
| 2014/0297201 | A1 | 10/2014 | Knorr et al. |
| 2014/0299577 | A1 | 10/2014 | Chung et al. |
| 2014/0326865 | A1 | 11/2014 | Pringle et al. |
| 2014/0353488 | A1* | 12/2014 | Takats .......... G01N 27/622 250/282 |
| 2014/0353489 | A1 | 12/2014 | Szalay et al. |
| 2015/0021469 | A1 | 1/2015 | Bajic |
| 2015/0048255 | A1 | 2/2015 | Jarrell |
| 2015/0087003 | A1 | 3/2015 | Charles et al. |
| 2015/0144782 | A1 | 5/2015 | Fogwill et al. |
| 2015/0192590 | A1 | 7/2015 | Sodeoka et al. |
| 2015/0201913 | A1 | 7/2015 | Takats |
| 2016/0002696 | A1 | 1/2016 | Galiano |
| 2016/0133450 | A1 | 5/2016 | Green et al. |
| 2016/0215322 | A1 | 7/2016 | Goodlett et al. |
| 2016/0247668 | A1 | 8/2016 | Szalay et al. |
| 2016/0341712 | A1 | 11/2016 | Agar |
| 2016/0372313 | A1 | 12/2016 | Brown et al. |
| 2017/0103880 | A1 | 4/2017 | Syage |
| 2018/0136091 | A1 | 5/2018 | Ryan et al. |

FOREIGN PATENT DOCUMENTS

| | | |
|---|---|---|
| CN | 101223625 A | 7/2008 |
| CN | 101288146 A | 10/2008 |
| CN | 101413905 A | 4/2009 |
| CN | 101490524 A | 7/2009 |
| CN | 201266145 Y | 7/2009 |
| CN | 101657158 A | 2/2010 |
| CN | 101819179 A | 9/2010 |
| CN | 101871914 A | 10/2010 |
| CN | 102026709 A | 4/2011 |
| CN | 102121921 A | 7/2011 |
| CN | 102137618 A | 7/2011 |
| CN | 102164675 A | 8/2011 |
| CN | 102264404 A | 11/2011 |
| CN | 102367424 A | 3/2012 |
| CN | 102445544 A | 5/2012 |
| CN | 102483369 A | 5/2012 |
| CN | 102800553 A | 11/2012 |
| CN | 102879453 A | 1/2013 |
| CN | 102924993 A | 2/2013 |
| CN | 102928610 A | 2/2013 |
| CN | 103295873 A | 9/2013 |
| CN | 103335984 A | 10/2013 |
| CN | 103597574 A | 2/2014 |
| CN | 104254772 A | 12/2014 |
| CN | 104254901 A | 12/2014 |
| CN | 104582616 A | 4/2015 |
| EP | 0169469 A2 | 1/1986 |
| EP | 0437358 A2 | 7/1991 |
| EP | 1855306 A1 | 11/2007 |
| EP | 1730519 B1 | 7/2010 |
| EP | 3265818 B1 | 2/2012 |
| EP | 3265817 A1 | 1/2018 |
| EP | 3266035 A1 | 1/2018 |
| GB | 2425178 A | 10/2006 |
| GB | 2491486 A | 12/2012 |
| JP | S63243864 A | 10/1988 |
| JP | 03001435 A | 8/1991 |
| JP | H0785834 A | 3/1995 |
| JP | H07130325 A | 5/1995 |
| JP | 10302710 A | 4/1997 |
| JP | H10247472 A | 9/1998 |
| JP | H11164283 A | 3/1999 |
| JP | 2000097913 A | 4/2000 |
| JP | 2000180413 A | 6/2000 |
| JP | 2001183345 A | 7/2001 |
| JP | 2002170518 A | 6/2002 |
| JP | 2004264043 A | 6/2002 |
| JP | 2005205181 A | 8/2005 |
| JP | 2006329710 A | 12/2006 |
| JP | 2007051934 A | 3/2007 |
| JP | 2007170870 A | 7/2007 |
| JP | 2007218916 A | 8/2007 |
| JP | 2010169454 A | 8/2010 |
| JP | 2014515831 A | 7/2014 |
| JP | 2015503109 A | 1/2015 |
| JP | 2015504160 A | 2/2015 |
| KR | 1020020013544 A | 4/2007 |
| KR | 1020100106336 A | 10/2010 |
| WO | 9734534 A1 | 9/1997 |
| WO | 0160265 A1 | 8/2001 |
| WO | 2008148557 A2 | 12/2008 |
| WO | 2010075265 A2 | 7/2010 |
| WO | 2010136887 A1 | 12/2010 |
| WO | 2011114902 A1 | 9/2011 |
| WO | 20120143737 A1 | 10/2012 |
| WO | 2012164312 A2 | 12/2012 |
| WO | 2012174437 A1 | 12/2012 |
| WO | 2013098642 A2 | 7/2013 |
| WO | 2013098645 A2 | 7/2013 |
| WO | 2013102670 A1 | 7/2013 |
| WO | 2013/148162 | 10/2013 |
| WO | 2013148162 A1 | 10/2013 |
| WO | 2014106165 A | 7/2014 |
| WO | 2014128629 A1 | 8/2014 |
| WO | 2014140601 A1 | 9/2014 |
| WO | 2014142926 A1 | 9/2014 |
| WO | 2014202828 A1 | 12/2014 |
| WO | 2015004457 A1 | 1/2015 |
| WO | 2015132579 A1 | 9/2015 |
| WO | 2016046748 A1 | 3/2016 |
| WO | 2016142674 A1 | 9/2016 |
| WO | 2016156615 A1 | 10/2016 |

OTHER PUBLICATIONS

Chen et al., "Surface desorption atmospheric pressure chemical ionization mass spectrometry for direct ambient sample analysis without toxic chemical contamination", Journal of Mass Spectrometry, 42(8):1045-1056, Jan. 1, 2007.

Chen, H., et al: "Neutral desorption sampling coupled to extractive electrospray ionization mass spectrometry for rapid differentiation of biosamples by metabolomic fingerprinting", Journal of Mass Spectromety, vol. 42, No. 9, Sep. 1, 2007 pp. 1123-1135.

Hensman C., et al: "Chemical Composition of Smoke Produced by High-Frequency Electrosurgery in a Closed Gaseous Environment an in Vitro Study", Surgical Endoscopy, vol. 12, No. 8, Aug. 1, 1998 (Aug. 1, 1998), pp. 1017-1019.

Moot, A. et al: "Composition of Volatile Organic Compounds in Diathermy Plume as Detected by Selected Ion Flow Tube Mass Spectrometry", ANZ Journal of Surgery, vol. 77, No. 1-2, (Jan. 2007) pp. 20-23.

Strittmatter, N.: "Home—Miss Nicole Strittmatter"Retrieved from the Internet URL: http://www.imperial.ac.uk/people/n.strittmatter12 [retrieved on May 19, 2016] the whole document.

Wehofsky, et al "Automated deconvolution and deisotoping of electrospray mass spectra" J. Mass Spectrom. 2002; 37: pp. 223-229.

Al Sahaf et al., "Chemical Composition of Smoke Produced by High-Frequency Electrosurgery", Irish Journal of Medical Science, vol. 176, No. 3, pp. 229-232, 2007.

Barrett et al., "Surgical Smoke: A Review of the Literature", Surgical Endoscopy, vol. 17, No. 6, pp. 979-987, 2003.

Down, "A DESI-Rable Ionization Revolutionizes Mass Spectrometry", Base Peak, 2005.

(56) References Cited

OTHER PUBLICATIONS

International Search Report and Written Opinion for International Application. No. PCT/IB2012/003009, dated Aug. 14, 2013, 17 pages.
PCT International Search Report and Written Opinion for International Appln. No. PCT/IB2010/001261, dated Sep. 21, 2010, 5 pages (MDMSS.00INP).
PCT International Search Report and Written Opinion for International Appln. No. PCT/IB2012/002995, dated Sep. 10, 2013, 3 pages (MDMSS.005WO).
Qiao et al., "Electrostatic-Spray Ionization Mass Spectrometry", Analytical Chemistry, vol. 84, No. 17, pp. 7422-7430, 2012.
Lee et al., "Thermally Assisted Electrospray Interface for Liquid Chromatography/Mass Spectrometry", Rapid Communications in Mass Spectrometry, vol. 6, pp. 727-733, 1992.
McEwen et al., "Analysis of Solids, Liquids, and Biological Tissues Using Solids Probe Introduction at Atmospheric Pressure on Commercial LC/MS Instruments", Anal. Chem., vol. 77, pp. 7826-7831, 2005.
Sakairi et al., "Characteristics of a Liquid Chromatograph/Atmospheric Pressure Ionization Mass Spectrometer", Anal. Chem., vol. 60, pp. 774-780, 1988.
Takats et al., "Characterization of DESI-FTICR Mass Spectrometry—From ECD to Accurate Mass Tissue Analysis", Journal of Mass Spectrometry, vol. 43, pp. 196-203, 2008.
Eagles, et al., "Fast Atom Bombardment Mass Spectrometry of Amine Mixtures", John Wiley & Sons, Ltd, 1988.
Slemr et al., Concentration Profiles of Diamines in Fresh and aerobically Stored Park and Beef, American Chemical Society, 1985.
Mulligan, Christopher C. et al., "Desorption electrospray ionization with a portable mass spectrometer: in situ analysis of ambient surfaces", Chemical Communications—Chemcom, No. 16, pp. 1709-1711, (Jan. 2006).
Van Berkel, "Thin-Layer Chromatography and El3ectrospray Mass Spectrometry Coupled Using a Surface Sampling probe". Anal. Chem. 2002.
Takats et al., "Mass Spectrometry Sampling Under Ambient Conditions with Desorption Electrospray Ionization", Science, vol. 306, 2004.
Tottszer et al., "Laser Heating Versus Resistive Heating in the Field-Desorption Mass Spectrometry of Organic Polymers", J. Phys. D: Appl. Phys., vol. 21, pp. 1713-1720, 1988.
Zhou, X. et al., "Development of miniature mass spectrometry systems for bioanalysis outside the conventional laboratories." Bioanalysis, 6 (11) 1497-1508 (2014).
Bolt, F., et al., "Automated High-Throughput Identification and Characterization of Clinically Important Bacteria and Fungi using Rapid Evaporative Ionization Mass Spectrometry," American Chemical Socieity, 88 9419-9426 (2016).
McJimpsey, E.L., et al., "Parameters Contributing to Efficient Ion Generation in Aerosol MALDI Mass Spectrometry," American Society for Mass Spectrometry pp. 1044-0305 (2007).
Mutters, N.T., et al., "Performance of Kiestra Total Laboratory Automation Combined with MS in Clinical Microbiology Pactice," Annals of Laboratory Medicine 34: 111-117 (2014).
Longuespée, R., et al., Tissue Proteomics for the Next Decade? Towards a Molecular Dimension in Histology, OMICS A Journal of Integrative Biology 28(9): 539-552 (2014).
Lu, K., et al., "Arsenic Exposure Perturbs the Gut Microbiome and its Metabolic Profile in Mice: An Integrated Metagenomics and Metabolomics Analysis," Environmental Health Perspectives, 122(3): 284-291 (2014).
Suarez, S., et al., Ribosomal proteins as biomarkers for bacterial identification by mass spectrometry in the clinical microbiology laboratory, Journal of microbiological Methods, 94: 390-396 (2013).
Trimpin, S. et al., New Ionization Method for Analysis on Atmospheric Pressure Ionization Mass Spectrometers Requiring Only Vacuum and Matrix Assistance, Analytical Chemistry, 85:2005-2009 (2013).
Cha, S., Laser desorption/ionization mass spectrometry for direct profiling and imaging of small moledcules from raw biological materials, Doctoral Dissertation, Iowa State University (2008).
Asano et al., "Self-aspirating atmospheric pressure chemical ionization source for direct sampling of analytes on Surfaces in liquid solution", Rapid Communications in Mass Spectrometry 2005.
nternational Search Report and Written Opinion for application No. PCT/GB2017/051050, dated Jun. 27, 2017, 15 pages.
Gerbig, Stefanie et al, "Spatially resolved investigation of systemic and contact pesticides in plant material by desorption electrospray ionization mass spectrometry imagine", Analytical and Bioanalytical Chemistry, 407(24):7379-7389 (2015).
Lesiak, A., et al.,"Rapid detection by direct analysis in real time-mass spectrometry (DART-MS) of psychoactive plant drugs of abuse: the case of Mitragyna speciosa aka "Kratom"", 242:210-218 (2014).
Bartels, B. et al., "Spatially resolved in vivo plant metabolomics by laser ablation-based mass spectrometry imaging (MSI) techniques: LDI-MSI and LAESI", Frontiers in Plant Science vol. 6 (2015).
Nielen, M et al., "Desorption electrospray ionization mass spectrometry in the analysis of chemical food contaminants in food", Trac Trends in Analytical Chemistry, 30(2):165-180 (2011).
Boughton, B. et al., "Mass spectrometry imaging for plant biology: a review", Phytochemistry Reviews, 15(3):445-488 (2015).
Schäfer, K.C., et al., "In Situ, Real-Time Identification of Biological Tissue by Ultraviolet and Infrared Laser Desorption Ionization Mass Spectrometry", Analytical Chemistry, 83(5):1632-1640, Mar. 1, 2011.
International Search Report and Written Opinion for International Application No. PCT/GB2016/052956, dated Jan. 26, 2017, 16 pages.
Hsu, et al., "Microscopy ambient ionization top-down mass spectrometry reveals developmental patterning", Proceedings of the National Academy of Sciences, vol. 110, No. 37, pp. 14855-14860, Aug. 22, 2013.
Na, et al., "Development of a Dielectric Barrier Discharge Ion Source for Ambient Mass Spectrometry", Journal of the American Society for Mass Spectrometry, Elsevier Science Inc, vol. 18, No. 10, pp. 1859-1862, Sep. 20, 2007.
Ellis, S. et al., "Surface Analysis of Lipids by Mass Spectrometry: More Than Just Imaging", Progress in Lipid Research Pergamon Press, vol. 52, No. 4, pp. 329-353 (Oct. 2013).
Dong, Y., et al., "Sample Preparation for Mass Spectrometry Imaging of Plant Tissues: A Review", Frontiers in Plant Science 7(60): 1-16 (2016).
Communication pursuant to Article 94(3) EPC, for application No. 16710788.7, dated Jun. 13, 2019, 9 pages.
Examination Report under Section 18(3), for application No. GB1714122.7, dated May 9, 2019, 6 pages.
Bagley, B.M., et al., "Evaluation of archival time on shotgun proteomics of formalin-fixed and paraffin-embedded tissues", Journal of Proteome Research 8(2):917-925, (2009).
Cho, YT., et al. "Differentiation of Virulence of Helicobacter Pyloriby Matrix-Assited Laser Desorption/Ionization Mass Spectrometry and Multivariate Analyses" Clinica Chimica ACTA, Elsevier BV, 424:123-130, May 26, 2013.
Agar, Nathalie et al., "*Development of Stereotactic Mass Spectrometry for Brain Tumor Surgery*", Biosis, Neurosurgery Online, vol. 68, No. 2, (2011).
Ahlf, Dorothy R. et al., "*Correlated Mass Spectrometry Imaging and Confocal Raman Microscopy for Studies of Three-Dimensional Cell Culture Sections*", Analyst, vol. 139, No. 18, pp. 4578 (2014).
Azimzadeh, Omid et al., "*Formalin-Fixed Paraffin-Embedded (FFPE) Proteome Analysis Using Gel-Free and Gel-Based Proteomics*", Journal of Proteome Research, vol. 9, No. 9, pp. 4710-4720 (2010).
Balgley, Brian M. et al., "*Evaluation of Archival Time on Shotgun Proteomics of Formalin-Fixed and Paraffin-Embedded Tissues*", Journal of Proteome Research, vol. 8, No. 2, pp. 917-925 (2009).
Balog, Julia et al., "*Identification of Biological Tissues by Rapid Evaporative Ionization Mass Spectrometry*", Analytical Chemistry, vol. 82, No. 17, pp. 7343-7350 (2010).

(56) References Cited

OTHER PUBLICATIONS

Balog, Julia et al., "Supporting Information for Identification of Biological Tissues by Rapid Evaporative Ionization Mass Spectrometry", pp. S1-S9, http://pubs.acs.org/doi/suppl/10.1021/ac101, (2013).

Balog, J. et al., "Intraoperative Tissue Identification Using Rapid Evaporative Ionization Mass Spectrometry", Science Translational Medicine, vol. 5, No. 194, pp. 194ra93 (2013).

Balog, J. et al., "Supplementary Materials: Intraoperative Tissue Identification Using Rapid Evaporative Ionization Mass Spectrometry", Science Translational Medicine, vol. 5, No. 194, pp. 194ra93 (2013).

Bean, Heather D. et al., "Bacterial Volatile Discovery Using Solid Phase Microextraction and Comprehensive Two-Dimensional Gas Chromatographytime-of-Flight Mass Spectrometry", Journal of Chromatography B, vol. 901, pp. 41-46 (2012).

Bellet, V. et al., "Proteomic Analysis of RCL2 Paraffin-Embedded Tissues", Journal of Cellular and Molecular Medicine, vol. 12, No. 5B, pp. 2027-2036 (2008).

Bocklitz, T.W. et al., "Deeper Understanding of Biological Tissue: Quantitative Correlation of MALDI-TOF and Raman Imaging", Analytical Chemistry, vol. 85, No. 22, pp. 10829-10834 (2013).

Cole, Laura M. et al., "Mass Spectrometry Imaging for the Proteomic Study of Clinical Tissue", Proteomics-Clinical Applications, vol. 9, No. 3-4, pp. 335-341 (2015).

Crawshaw, Benjamin et al., "Gastrointestinal Surgery: Real-Time Tissue Identification During Surgery", Nature Review/ Gastroenterology & Hepatology Nature, vol. 10, No. 11. pp. 624-625.

Cselik, Z. et al., "Impact of Infrared Laser Light-Induced Ablation at Different Wavelengths on Bovine Intervertebral Disc Ex Vivo: Evaluation with Magnetic Resonance Imaging and Histology", Lasers in Surgery and Medicine, vol. 44, No. 5, pp. 406-412 (2012).

Davies, T.J. et al., "Volatile Products front Acetylcholine as Markers in the Rapid Urine Test Using Head-Space Gas-Liquid Chromatography B: Biomedical Sciences and Applications", Journal of Chromatography, vol. 307, pp. 11-21 (1984).

European Commission, "ISD Report Summary", http://cordis.europa.eu/result/rcn/163435_e, (2016).

Fahy, Eoin, et al., "Lipid Classification, Structures and Tools", Biochimica at Biophysica Acta (BBA)—Molecular and Cell Biology of Lipids, vol. 1811, No. 11, pp. 637-647 (2011).

Gerbig, Stefanie et al., "Analysis of Colorectal Adenocarcinoma Tissue by Desorption Electrospray Ionization Mass Spectrometric Imaging", Analytical and Bioanalytical Chemistry, vol. 403, No. 8, pp. 2315-2325 (2012).

Golf, Ottmar et al., "Rapid Evaporative Ionization Mass Spectrometry Imaging Platform for Direct Mapping front Bulk Tissue and Bacterial Growth Media", Analytical Chemistry, vol. 87, No. 5, pp. 2527-2534 (2015).

Golf, Ottmar et al., "XMS: Cross-Platform Normalization Method for Multimodal Mass Spectrometric Tissue Profiling", Journal of the American Society for Mass Spectrometry, vol. 26, No. 1, pp. 44-54 (2014).

Guenther, Sabine et al., "Electrospray Post-Ionization Mass Spectrometry of Electrosurgical Aerosols", Journal of the American Society for Mass Spectrometry, vol. 22, No. 11, pp. 2082-2089 (2011).

Gustafsson, Ove J.R. et al., "Proteomic Developments in the Analysis of Formalin-Fixed Tissue", Biochimica et Biophysica Acta, vol. 1854, No. 6, pp. 559-580.

Hobbs, S.K. et al., "Magnetic Resonance Image-Guided Proteomics of Human Glioblastoma Multiforme", Journal of Magnetic Resonance Imaging, vol. 18, pp. 530-536 (2003).

Hsu, Cheng-Chih et al., "Visualizing Life with Ambient Mass Spectrometry", Current Opinion in Biotechnology, vol. 31, pp. 24-34 (2015).

Jadoul, L. et al., "Matrix-Assisted Laser Desorption/Ionization Mass Spectrometry and Raman Spectroscopy: An Interesting Complementary Approach for Lipid Detection in Biological Tissues", European Journal of Lipid Science and Technology. vol. 116, No. 8, pp. 1080-1086 (2014).

Jain, M. et al., "Metabolite Profiling Identifies a Key Role for Glycine in Rapid Cancer Cell Proliferation", American Association for the Advancement of Science, vol. 336, No. 6084, pp. 1040-1044 (2012).

Jarmusch, Alan K et al., "Detection of Strep Throat Causing Bacterium Directly front Medical Swabs by Touch Spray-Mass Spectrometry", Analyst, vol. 139, No. 19, pp. 4785 (2014).

Jarmusch, Alan K. et al., "Supplemental Information Detection of Strep Throat Causing Bacterium Directly from Medical Swabs by Touch Spray-Mass Spectrometry", http://www.rsc.org/suppdata/an/c4/c4an00959 (2016).

Lazova, Rossitza et al., "Imaging Mass Spectrometry—A New and Promising Method to Differentiate Spitz Nevi From Spitzoid Malignant Melanomas", American Journal of Dermatopathology, vol. 34, No. 1, pp. 82-90 (2012).

Li, Yan et al., "Aberrant Mucin5B Expression in Lung Adenocarcinomas Detected by iTRAQ Labeling Quantitative Proteomics and Immunohistochemistry", Clinical Proteomics, vol. 10, No. 1, pp. 15 (2013).

Lieuwe, D.J. et al., "Volatile Metabolites of Pathogens: A Systematic Review", PLoS Pathogens, vol. 9, No. 5, pp. 1003311.

Luge, S. et al., "Use of a Lower Power, High Frequency Stabilized Capacitive Plasma Combined with Graphite Furnace Vaporization for the Atomic Emission Spectrometric Analysis of Serum Samples", Analytical Chimica Acta, vol. 332, No. 2-3, pp. 193-199 (1996).

Mccullough, Bryan J. et al., "On-Line Reaction Monitoring by Extractive Electrospray Ionisation", Rapid Communications in Mass Spectrometry, vol. 25, No. 10, pp. 1445-1451 (2011).

Murray, Patrick R, "What Is New in Clinical Microbiology-Microbial Identification by MALDI-TOF Mass Spectrometry", Journal of Molecular Diagnostics, vol. 14, No. 5, pp. 419-423 (2012).

Nicholson, Jeremy K. et al., "Metabolic Phenotyping in Clinical and Surgical Environments", Nature, vol. 491, No. 7424 pp. 384-392 (2012).

Pirro, Valentina et al., "Direct Drug Analysis from Oral Fluid Using Medical Swab Touch Spray Mass Spectrometry", Analytica Chimica Acta, vol. 861, pp. 47-54.

Plata, N. et al., "Aerosols Sampling Using a New Cryogenic Instrument", Journal of Aerosol Science, vol. 37, No. 12, pp. 1871-1875 (2006).

Rodriguez-Rigueiro, Teresa et al., "A Novel Procedure for Protein Extraction from Formalin-Fixed Paraffin-Embedded Tissues", Proteomics, vol. 11, No. 12, pp. 2555-2559 (2011).

Schafer, Karl-Christian et al., "In Vivo, In Situ Tissue Analysis Using Rapid Evaporative Ionization Mass Spectrometry", Angewandte Chemie International, vol. 48, No. 44, pp. 8240-8242 (2009).

Shane, Ellis R. et al., "Surface Analysis of Lipids by Mass Spectrometry: More Than Just Imaging", Progress in Lipid Research Pergamon Press, vol. 52, No. 4, pp. 329-353.

Shoemaker, Robert H., "The NCI60 Human Tumour Cell Line Anticancer Drug Screen", (2013).

Strittmatter, N. et al., "Anaylsis of Intact Bacteria Using Rapid Evaporative Ionisation Mass Spectrometry", Chemical Communications, vol. 49, No. 55, pp. 6188 (2013).

Strittmatter, N. et al., "Characterization and Identification of Clinically Relevant Microorganisms Using Rapid Evaporative Ionization Mass Spectrometry", Analytical Chemistry, vol. 86, No. 13, pp. 6555-6562 (2014).

Strittmatter, N. et al., "Taxon-Specific Markers for the Qualitative and Quantitative Detection of Bacteria in Human Samples", http://www.msacl.org/2015_US_Long_Abstract.

Tait, Emma et al., "Identification of Volatile Organic Compounds Produced by Bacteria Using HS-SPME-GC-MS", Journal of Chromatographic Sci, pp. 1-11.

Uribe, D.O. et al., "Piezoelectric Self-Sensing System for Tactile Intraoperative Brain Tumor Delineation in Neurosurgery", Proceedings of the 31$^{st}$ Annual International Conference of the IEEE Engineering in Medicine and Biology Society: Engineering the Future of BioMedicine, pp. 737-740 (2009).

(56) References Cited

OTHER PUBLICATIONS

Vander Wilp, W. et al., "*Lead in Micro-Samples of Whole Blood by Rhenium-Cup in-Torch Vaporization-Inductively Coupled Plasma-Atomic Emission Spectrometry* (ITV-ICP-AES)", Fresenius' Journal of Analytical Chemistry, vol. 368, No. 7, pp. 734-736 (2000).
Vircks, Kyle E. et al., "*Rapid Screening of Synthetic Cathinones as Trace Residues and in Authentic Seizures Using a Portable Mass Spectrometer Equipped with Desorption Electrospray Ionization*", Rapid Communications in Mass Spectrometry, vol. 26, No. 23, pp. 2665-2672 (2012).
Kohler, M. et al. "Characterization of lipid extracts from brain tissue and tumors using Raman spectroscopy and mass spectrometry," Anal Bioana Chem, 393:1513-1520, Jan. 20, 2009.
Harry, K. H., et al. "Effect of protein coating of flocked swabs on the collection and release of clinically important bacteria", Indian Journal of Medical Microbiology, 32(3):301-303 (2014).
Blais, B. W., "Swab-Based Enzyme Immunoassay System for Detection of Meat Residues on Food Contact Surfaces as a Hygiene Monitoring Tool", Journal of Food Protection, 62(4):386-389 (1999).
Farhat S. E. et al., "Efficacy of a Swab Transport System in Maintaining Viability of Neisseria gonorrhoeae and *Streptococcus pneumoniae*", Journal of Clinical Microbiology, 39(8):2958-2960 (2001).
Hachmoeller et al., "Element bioimaging of liver needle biopsy specimens from patients with Wilsons disease by laser ablation-inductively coupled plasma-mass spectrometry", Journal of Trace Elements in Medicine and Biology, 35:97-102, Feb. 10, 2016.
Guenther et al., "Spatially Resolved Metabolic Phenotyping of Breast Cancer by Desorption Electrospray Ionization Mass Spectrometry", Cancer Research, 75:1828-1837, Feb. 17, 2015.
Santagata, S., et al., "Intraoperative mass spectrometry mapping of an onco-metabolite to guide brain tumor surgery", Proceedings of the National Academy of Sciences (PNAS), 111(30):11121-11126, Jun. 30, 2014.
Chipuk, J. E., et al., "Transmission Mode Desorption Electrospray Ionization", Journal of the American Society for Mass Spectrometry, 19(11):1612-1620, Nov. 1, 2008.
Harry, E. L. et al., "Direct analysis of pharmaceutical formulations from non-bonded reversed-phase thin-layer chromatography plates by desorption electrospray ionisation ion mobility mass spectrometry", Rapid Communications in Mass Spectrometry, 23(17):2597-2604, Jul. 28, 2009.
Chen, H., et al., "What Can We Learn from Ambient Ionization Techniques", Journal of the American Society for Mass Spectrometry, 20:1947-1963, (2009).
Sankaranarayanan, G., et al., "Common Uses and Cited Complications of Energy in Surgery", Surg Endosc., 27:3056-3072, (2013).
Rau, H.G., et al., "The use of water-jet dissection in open and laparoscopic liver resection", HPB, 10:275-280, (2008).
Chen et al. "Desorption Electrospray Ionization Mass spectrometry for high-thoughput analysis of Pharamaceutical samples in the ambient environment" (Year: 2005).
Office Action for CN Patent Application No. 201680025801.0 dated Apr. 7, 2020.
Office Action for CN Patent Application No. 201680025801.0 dated Apr. 7, 2020 [translation].
Adams, F., et al, "Inorganic Mass Spectrometry", copyright John Wiley Sons, Inc. pp. 174-180 (1988).
Jackson, S. N. et al. On-line laser desorption/ionization mass spectrometry of matrix-coated aerosols, Rapid Communications in Mass Spectrometry, vol. 18, pp. 2041-2045 (Year 2004).
Vemury, S., and Pratsinis, S.E., "Charging and Coagulation During Flame Synthesis of Silica", Journal of Aerosol Science 27(6):951-966 (1996).
Examination Report under Section 18(3), for application No. GB1715787.6, dated Jun. 1, 2020, 6 pages.
CNOA 201680026285.3 dated Jun. 12, 2020, 12 pages.
Panpradist, N., et al., "Swab Sample Transfer for Point-Of-Care Diagnostics: Characterization of Swab types and Manual Agitation Methods", Plos One 9(9):1-11 (2014).

Jartial European Search Report for EP20181905.9, dated Aug. 27, 2020, 14 pages.
Roddy, T., et al., "Imaging of Freeze-Fractured Cells with in Situ Fluorescence and Time-of-Flight Secondary Ion Mass Spectrometry", Analytical Chemistry 74(16):4011-4019 (2002).
Petrotchenko, E.V., et al., "Combining Fluorescence Detection and Mass Spectrometric Analysis for Comprehensive end Quantitative Analysis of Redox-Sensitive Cysteines in Native Membrane Proteins", Analytical Chemistry 78(23):7959-7966 (2006).
Ablonczy, Z., et al., "The utilization of fluorescence to identify the components of lipofuscin by imaging mass spectrometry", Proteomics 14(7-8):936-944.
Enthaler, B., et al., "Improved sample preparation for MALDI-MSI of endogenous compounds in skin tissue sections and mapping of exogenous active compounds subsequent to ex-vivo skin penetration" Anal Bioanal Chem 402:1159-1167 (2012).
Extended EP search report for EP Application No. 20172634.6, dated Sep. 14, 2020, 8 pages.
CNOA for application No. CN2016800258010 dated Oct. 12, 2020 for 8185.0185 corresponding app original document and translation.
Adams, F., et al., "Inorganic Mass Spectrometry", (1993) Abstract.
Dong, Y.M.B.A., "Polymer Analysis Handbook", China Petromchemical Press (2004) 8 pages.
Waters DESI System Operators Guide 715004701/Revision A, Waters Corporation, [online] Jan. 2015 [retrieved on Dec. 3, 2020]. Retrieved from Internet URL: https://www.waters.com/webassets/cms/support/docs/715004701ra. pdf. 141 pages.
Shin, Y-S., et al., "Desorption Electrospray Ionization-Mass Spectrometry of Proteins" Analytical Chemistry 79:3514-3518 (2007).
Chen, X., ed. "Liquid Chromatography-Mass Spectrometry—Chapter 8", in Principle and Application of Chromatographic Analysis Technology, Chinese Peoples Public Security University Press, (Jan. 2014) 6 pages.
Song, Y. et al. "Rapid ambient mass spectrometric profiling of intact, untreated bacteria using desorption electrospray ionization" ChemComm pp. 61-63 (2007).
Wiseman, J.M. And Li, J.B., "Elution, Partial Separation, and Identification of Lipids Directly from Tissue Slices on Planar Chromatography Media by Desorption Electrospray Ionization Mass Spectrometry", Anal Chem 82:8866-8874 ,2010).
Search and Examination Report under Sections 17 and 18(3) for GB1715767.8, dated Nov. 26, 2020, 6 pages.
Krouskop, T., et al., Ultrasonic Imaging, vol. 20, 1998, "Elastic moduli of breast and prostate tissues under compression" Ultrasonic Imaging 20:260-274 (1998).
Aberg, P., et al., "Skin Cancer Identification Using Multifrequency Electrical Impedance—A Potential Screening Tool", IEEE Transactions on Biomedical Engineering, 51(12): 2097-2102 (2004).
Examination Report under Section 18(3) for Application No: GB2015580.0, dated Jan. 21, 2021, 4 pages.
Rath, C.M., et al., "Molecular Analysis of Model Gut Microbiotas by Imaging Mass Spectrometry and Nanodesorption Electrospray Ionization Reveals Dietary Metabolite Tranformations" Analytical Chemistry 84(21):9259-9267 (2012).
Fenselau, C.C., "Rapid Characterization of Microorganisms by Mass Spectrometry—What Can Be Learned and How?" Journal of the American Society for Mass Spectrometry 24(8):1161-1166 (2013).
Uetrecht, C. et al., "Modern Biomolecular Mass Spectrometry and its Role in Studying Virus Structure, Dynamics and Assembly" Angewandte Chemie International Edition 50(36):8248-8262 (2011).
Forbes, T.P. et al., "Chemical imaging of artificial Fingerprints by desorption electro-flow focusing ionization mass spectrometry" Analyst 139(12):2982-2985 (2014).
Cornett, D. S., et al, "A Novel Histology-directed Strategy for MALDI-MS Tissue Profiling That Improves Throughput and Cellular Specificity in Human Breast Cancer", American Society for Biochemistry and Molecular Biology, pp. 1975-1983, Jul. 18, 2006.
Extended European Search Report for Application No. 20210062.4, dated Mar. 9, 2021, 13 pages.
Examination Report under Section 18(3) for Application No. GB1715750.4 dated Mar. 22, 2021, 5 pages.

(56) References Cited

OTHER PUBLICATIONS

Examination Report for GB Patent Application No. GB2015580.0, dated Mar. 12, 2021, 4 pages.
Examination Report under Section 18(3) for Application No. GB1714165.6, dated Mar. 22, 2021, 6 pages.

* cited by examiner

PHYSICALLY GUIDED RAPID EVAPORATIVE IONISATION MASS SPECTROMETRY ("REIMS")

CROSS-REFERENCE TO RELATED APPLICATIONS

This application represents the U.S. National Phase of International Application number PCT/GB2016/050597 entitled "Physically Guided Evaporative Ionisation Mass Spectrometry ("REIMS")" filed 7 Mar. 2016, which claims priority from and the benefit of United Kingdom patent application No. 1503876.3 filed on 6 Mar. 2015, United Kingdom patent application No. 1503864.9 filed on 6 Mar. 2015, United Kingdom patent application No. 1518369.2 filed on 16 Oct. 2015, United Kingdom patent application No. 1503877.1 filed on 6 Mar. 2015, United Kingdom patent application No. 1503867.2 filed on 6 Mar. 2015, United Kingdom patent application No. 1503863.1 filed on 6 Mar. 2015, United Kingdom patent application No. 1503878.9 filed on 6 Mar. 2015, United Kingdom patent application No. 1503879.7 filed on 6 Mar. 2015 and United Kingdom patent application No. 1516003.9 filed on 9 Sep. 2015. The entire contents of these applications are incorporated herein by reference.

FIELD OF THE INVENTION

The present invention relates generally to the analysis of a target (which may, for example, comprise in vivo, ex vivo or in vitro tissue) by ambient ionisation techniques such as rapid evaporative ionisation mass spectrometry ("REIMS"), methods of analysis and diagnosis and apparatus for analysing a target using an ambient ionisation ion source. Various embodiments are contemplated wherein analyte ions generated by an ambient ionisation ion source are then subjected either to: (i) mass analysis by a mass analyser such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly ion mobility analysis (IMS) and/or differential ion mobility analysis (DMA) and/or Field Asymmetric Ion Mobility Spectrometry (FAIMS) analysis followed by secondly mass analysis by a mass analyser such as a quadrupole mass analyser or a Time of Flight mass analyser (or vice versa). Various embodiments also relate to an ion mobility spectrometer and/or mass analyser and a method of ion mobility spectrometry and/or method of mass analysis.

BACKGROUND

Rapid evaporative ionisation mass spectrometry ("REIMS") is a relatively new technique that is useful for the analysis of many different types of samples including the identification of tissue.

Reference is made to N. Strittmatter et al., Anal. Chem. 2014, 86, 6555-6562 which discloses an investigation into the suitability of using rapid evaporative ionisation mass spectrometry as a general identification system for bacteria and fungi.

The known approach for analysing bacterial colonies by rapid evaporative ionisation mass spectrometry involves using bipolar electrosurgical forceps and an electrosurgical RF generator. A bacterial colony is scraped from the surface of an agar layer using the bipolar electrosurgical forceps and a short burst of RF voltage from the electrosurgical RF generator is applied between the bipolar electrosurgical forceps. For example, it is known to apply 60 W of power in a bipolar mode at a frequency of 470 kHz sinusoid. The RF voltage which is applied to the electrosurgical forceps has the result of rapidly heating the particular portion of the bacterial colony which is being analysed due to its nonzero impedance. The rapid heating of the microbial mass results in an aerosol being generated. The aerosol is transferred directly into a mass spectrometer and the aerosol sample may then be analysed by the mass spectrometer. It is known for the control system of the mass spectrometer to utilise multivariate statistical analysis in order to help distinguish and identify different samples.

Brain cancers are one of the leading causes of cancer-related deaths in children and young adults. Surgical resection of primary brain tumours is still the most often used therapy. However, in many cases the complete removal of the cancer is very difficult without damaging a vital function and it is problematic to accurately determine the margins of cancerous tissue when performing a resection of a brain tumour.

It is desired to provide an improved method of analysing a target or tissue using an ambient ionisation ion source.

SUMMARY

According to an aspect there is provided a method comprising:

obtaining or acquiring physical or other non-mass spectrometric data from one or more regions of a target; and using a first device to generate aerosol, smoke or vapour from one or more regions of the target.

In accordance with various embodiments physical non-mass spectrometric data may be obtained from a target (which may comprise in vivo tissue). For example, the target may be probed with a physical sensor and regions of interest in the target may be identified from the physical data output by the probe. A region of potentially cancerous tissue may be identified on the basis of having a higher surface hardness than that of surrounding tissue. The physical non-mass spectrometric data may then be used to direct a surgeon as to which tissue potentially needs to be resected.

A particularly beneficial aspect is that when an ambient ionisation source is used to generate aerosol, smoke or vapour from one or more regions of the target, the resulting aerosol, smoke or vapour may be ionised by directing the aerosol, smoke or vapour onto a collision surface within a vacuum chamber of a mass spectrometer and/or ion mobility spectrometer. The resulting analyte ions may then be analysed and ion mobility data and/or mass spectrometric data may be obtained.

The mass spectrometric data and/or ion mobility data may be analysed in real time and subjected to multivariate analysis enabling a determination to be made in real time as to whether or not the tissue which is currently being resected or otherwise analysed is cancerous or not. As a result, a surgeon is able to make an accurate determination of the disease state of any tissue which is being operated upon or resected and also the surgeon is able to make an accurate determination of the margins of the tumour. It will be readily apparent that it is particularly important when resecting a tumour to ensure that all cancerous tissue is removed whilst at the same time ensuring that as minimal amount of healthy tissue as possible is removed.

The ability, therefore, of acquiring physical non-mass spectrometric data of a target (e.g. tissue) and using this physical data to assist a surgeon when operating on a patient using a surgical tool such as a rapid evaporative ionisation mass spectrometry device enables an improved method of analysis to be performed with the result that a patient has a greater probability of a positive surgical outcome.

N. Strittmatter et al., Anal. Chem. 2014, 86, 6555-6562 does not disclose acquiring physical non-mass spectrometric data from a target such as in vivo tissue and does not disclose using physical non-mass spectrometric data to determine one or more regions of tissue which are of potential interest (i.e., regions of tissue which may be potentially cancerous tissue).

The method may further comprise using the physical non-mass spectrometric data or other non-mass spectrometric data to determine one or more regions of interest of the target.

The physical or other non-mass spectrometric data may comprise data selected from the group consisting of: (i) density data; (ii) impedance data; (iii) hardness data; (iv) surface hardness data; (v) tissue hardness data; (vi) tactile data; (vii) force data; (viii) radio-frequency absorbance data; (ix) microwave reflectance or transmission data; (x) dielectric property data; (xi) dielectric permittivity or conductivity data; (xxii) Young's modulus data; and (xxiii) capacitance or resistance data.

The first device may comprise or form part of an ambient ion or ionisation source or the first device may generate the aerosol, smoke or vapour for subsequent ionisation by an ambient ion or ionisation source or other ionisation source.

The target may comprise native or unmodified target material.

The native or unmodified target material may be unmodified by the addition of a matrix or reagent.

The first device may be arranged and adapted to generate aerosol, smoke or vapour from one or more regions of the target without the target requiring prior preparation.

The first device may comprise an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a focussed or unfocussed ultrasonic ablation device; (xxii) a microwave resonance device; and (xxiii) a pulsed plasma RF dissection device.

The step of using the first device to generate aerosol, smoke or vapour from one or more regions of the target may further comprise contacting the target with one or more electrodes.

The one or more electrodes may comprise a bipolar device or a monopolar device.

The one or more electrodes may comprise: (i) a monopolar device, wherein the apparatus optionally further comprises a separate return electrode; (ii) a bipolar device; or (iii) a multi phase RF device, wherein the apparatus optionally further comprises a separate return electrode or electrodes.

The one or more electrodes may comprise a rapid evaporation ionization mass spectrometry ("REIMS") device.

The method may further comprise applying an AC or RF voltage to the one or more electrodes in order to generate the aerosol, smoke or vapour.

The step of applying the AC or RF voltage to the one or more electrodes may further comprise applying one or more pulses of the AC or RF voltage to the one or more electrodes.

The step of applying the AC or RF voltage to the one or more electrodes may cause heat to be dissipated into the target.

The step of using the first device to generate aerosol, smoke or vapour from one or more regions of the target may further comprise irradiating the target with a laser.

The first device may be arranged and adapted to generate aerosol from one or more regions of the target by direct evaporation or vaporisation of target material from the target by Joule heating or diathermy.

The step of using the first device to generate aerosol, smoke or vapour from one or more regions of the target may further comprise directing ultrasonic energy into the target.

The aerosol may comprise uncharged aqueous droplets optionally comprising cellular material.

At least 50%, 55%, 60%, 65%, 70%, 75%, 80%, 85%, 90% or 95% of the mass or matter generated by the first device and which forms the aerosol may be in the form of droplets.

The first device may be arranged and adapted to generate aerosol wherein the Sauter mean diameter ("SMD", d32) of the aerosol may be in a range: (i) <5 μm; (ii) 5-10 μm; (iii) 10-15 μm; (iv) 15-20 μm; (v) 20-25 μm; or (vi) >25 μm.

The aerosol may traverse a flow region with a Reynolds number (Re) in the range: (i) <2000; (ii) 2000-2500; (iii) 2500-3000; (iv) 3000-3500; (v) 3500-4000; or (vi) >4000.

Substantially at the point of generating the aerosol, the aerosol may comprise droplets having a Weber number (We) selected from the group consisting of: (i) <50; (ii) 50-100; (iii) 100-150; (iv) 150-200; (v) 200-250(vi) 250-300; (vii) 300-350; (viii) 350-400; (ix) 400-450; (x) 450-500; (xi) 500-550; (xii) 550-600; (xiii) 600-650; (xiv) 650-700; (xv) 700-750; (xvi) 750-800; (xvii) 800-850; (xviii) 850-900; (xix) 900-950; (xx) 950-1000; and (xxi)>1000.

Substantially at the point of generating the aerosol, the aerosol may comprise droplets having a Stokes number ($S_k$) in the range: (i) 1-5; (ii) 5-10; (iii) 10-15; (iv) 15-20; (v) 20-25; (vi) 25-30; (vii) 30-35; (viii) 35-40; (ix) 40-45; (x) 45-50; and (xi) >50.

Substantially at the point of generating the aerosol, the aerosol may comprise droplets having a mean axial velocity selected from the group consisting of: (i) <20 m/s; (ii) 20-30 m/s; (iii) 30-40 m/s; (iv) 40-50 m/s; (v) 50-60 m/s; (vi) 60-70 m/s; (vii) 70-80 m/s; (viii) 80-90 m/s; (ix) 90-100 m/s; (x) 100-110 m/s; (xi) 110-120 m/s; (xii) 120-130 m/s; (xiii) 130-140 m/s; (xiv) 140-150 m/s; and (xv) >150 m/s.

The target may comprise biological tissue.

The biological tissue may comprise human tissue or non-human animal tissue.

The biological tissue may comprise in vivo biological tissue.

The biological tissue may comprise ex vivo biological tissue.

The biological tissue may comprise in vitro biological tissue.

The biological tissue may comprise: (i) adrenal gland tissue, appendix tissue, bladder tissue, bone, bowel tissue, brain tissue, breast tissue, bronchi, coronal tissue, ear tissue, esophagus tissue, eye tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, ureter tissue, urethra tissue, soft and connective tissue, peritoneal tissue, blood vessel tissue and/or fat tissue; (ii) grade I, grade II, grade III or grade IV cancerous tissue; (iii) metastatic cancerous tissue; (iv) mixed grade cancerous tissue; (v) a sub-grade cancerous tissue; (vi) healthy or normal tissue; or (vii) cancerous or abnormal tissue.

The first device may comprise a point of care ("POC"), diagnostic or surgical device.

The method may further comprise ionising at least some of the aerosol, smoke or vapour so as to generate analyte ions.

The method may further comprise directing or aspirating at least some of the aerosol, smoke or vapour into a vacuum chamber of a mass spectrometer and/or ion mobility spectrometer.

The method may further comprise ionising at least some the aerosol, smoke or vapour within a or the vacuum chamber of the mass spectrometer and/or ion mobility spectrometer so as to generate a plurality of analyte ions.

The method may further comprise causing the aerosol, smoke or vapour to impact upon a collision surface located within a vacuum chamber of the mass spectrometer and/or ion mobility spectrometer so as to generate a plurality of analyte ions.

The method may further comprise mass analysing and/or ion mobility analysing the analyte ions in order to obtain mass spectrometric and/or ion mobility data.

The method may further comprise mass analysing and/or ion mobility analysing the aerosol, smoke or vapour or ions derived from the aerosol, smoke or vapour in order to obtain mass spectrometric data and/or ion mobility data.

Various embodiments are contemplated wherein analyte ions generated by an ambient ionisation ion source are then subjected either to: (i) mass analysis by a mass analyser such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly ion mobility analysis (IMS) and/or differential ion mobility analysis (DMA) and/or Field Asymmetric Ion Mobility Spectrometry (FAIMS) analysis followed by secondly mass analysis by a mass analyser such as a quadrupole mass analyser or a Time of Flight mass analyser (or vice versa). Various embodiments also relate to an ion mobility spectrometer and/or mass analyser and a method of ion mobility spectrometry and/or method of mass analysis.

The method may further comprise analysing the mass spectrometric data and/or ion mobility data in order either: (i) to distinguish between healthy and diseased tissue; (ii) to distinguish between potentially cancerous and non-cancerous tissue; (iii) to distinguish between different types or grades of cancerous tissue; (iv) to distinguish between different types or classes of target material; (v) to determine whether or not one or more desired or undesired substances may be present in the target; (vi) to confirm the identity or authenticity of the target; (vii) to determine whether or not one or more impurities, illegal substances or undesired substances may be present in the target; (viii) to determine whether a human or animal patient may be at an increased risk of suffering an adverse outcome; (ix) to make or assist in the making a diagnosis or prognosis; and (x) to inform a surgeon, nurse, medic or robot of a medical, surgical or diagnostic outcome.

The step of analysing the mass spectrometric data and/or ion mobility data may comprise performing a supervised or unsupervised multivariate statistical analysis of the mass spectrometric data and/or ion mobility data.

According to an embodiment either: (i) the multivariate statistical analysis may comprise principal component analysis ("PCA"); (ii) the multivariate statistical analysis may comprise linear discriminant analysis ("LDA"); (iii) the multivariate statistical analysis may be performed by a neural network; (iv) the multivariate statistical analysis may be performed by a support vector machine; or (v) the multivariate statistical analysis may comprise subspace discriminant analysis.

The step of analysing the mass spectrometric data and/or ion mobility data may further comprise analysing a profile of the aerosol, smoke or vapour or a profile of ions derived from the aerosol, smoke or vapour.

The profile may be selected from the group consisting of: (i) a lipidomic profile; (ii) a fatty acid profile; (iii) a phospholipid profile; (iv) a phosphatidic acid (PA) profile; (v) a phosphatidylethanolamine (PE) profile; (vi) a phosphatidylglycerol (PG) profile; (vii) a phosphatidylserines (PS) profile; (viii) a phosphatidylinositol (PI) profile; or (ix) a triglyceride (TG) profile.

The method may further comprise using one or more impedance sensors to obtain the physical or other non-mass spectrometric data.

The method may further comprise using the one or more impedance sensors either: (i) to obtain the physical or other non-mass spectrometric data without the one or more impedance sensors physically contacting the target; or (ii) to obtain the physical or other non-mass spectrometric data by physically contacting the target with the one or more impedance sensors.

The method may further comprise determining a density, a density profile, an impedance or an impedance profile of one or more regions of the target.

The step of using the physical or other non-mass spectrometric data to determine one or more regions of interest may comprise determining one or more regions of the target which have a different density or impedance relative to normal tissue, surrounding tissue, a control sample, a control region, control data or predetermined data.

The step of using the physical or other non-mass spectrometric data to determine one or more regions of interest may comprise determining whether or not a region of the target has a higher or lower density or impedance relative to normal tissue, surrounding tissue, a control sample, a control region, control data or predetermined data.

The method may further comprise using one or more force or tactile sensors to obtain the physical or other non-mass spectrometric data.

The method may further comprise using the one or more force or tactile sensors to obtain the physical or other non-mass spectrometric data by physically contacting the target with the one or more force or tactile sensors.

The method may further comprise determining a density, a density profile, a force, a force profile, a surface hardness or a surface hardness profile of one or more regions of the target.

The step of using the physical or other non-mass spectrometric data to determine one or more regions of interest may comprise determining one or more regions of the target which have a different density or surface hardness relative to normal tissue, surrounding tissue, a control sample, a control region, control data or predetermined data.

The step of determining from the physical or other non-mass spectrometric data one or more regions of interest of the target may comprise determining whether or not a region of the target has a higher or lower density or surface hardness relative to normal tissue, surrounding tissue, a control sample, a control region, control data or predetermined data.

The method may further comprise using one or more radio-frequency ("RF") or microwave sensors to obtain the physical or other non-mass spectrometric data.

The method may further comprise using the one or more radio-frequency ("RF") or microwave sensors either: (i) to obtain the physical or other non-mass spectrometric data without the one or more one or more radio-frequency ("RF") or microwave sensors physically contacting the target; or (ii) to obtain the physical or other non-mass spectrometric data by physically contacting the target with the one or more one or more radio-frequency ("RF") or microwave sensors.

The method may further comprise determining a density, a density profile, a radio-frequency absorbance, a radio-frequency absorbance profile, a microwave reflectance or transmission, a microwave reflectance or transmission profile, a dielectric property, a dielectric property profile, a dielectric permittivity, a dielectric permittivity profile, a conductivity or a conductivity profile of one or more regions of the target.

The step of using the physical or other non-mass spectrometric data to determine one or more regions of interest may comprise the use of targeted nanoparticles containing or comprising a metal which is intended to change the electrical impedance of a targeted tissue type. As detailed below, metallic nanoparticles may be functionalised so that they adhere to specific types of tissue or other surfaces. One or more regions of interest of a target may be identified by determining one or more regions of a target (e.g., tissue) having a different impedance to other target areas due to the presence of targeted or functionalised nanoparticles which preferentially adhere to certain specific target areas (e.g., cancerous tissue).

The step of using the physical or other non-mass spectrometric data to determine one or more regions of interest may comprise determining whether a region of the target has a different density, radio-frequency absorbance, microwave reflectance or transmission, dielectric property, permittivity or conductivity relative to normal tissue, surrounding tissue, a control sample, a control region, control data or predetermined data.

The step of using the physical or other non-mass spectrometric data to determine one or more regions of interest may comprise determining whether or not a region of the target has a higher or lower density, radio-frequency absorbance, microwave reflectance or transmission, dielectric property, permittivity or conductivity relative to normal tissue, surrounding tissue, a control sample, a control region, control data or predetermined data.

The method may further comprise using one or more dielectric property sensors or capacitive sensors to obtain the physical or other data.

The method may further comprise using the one or more dielectric property sensors or capacitive sensors either: (i) to obtain the physical or other non-mass spectrometric data without the one or more one or more dielectric property sensors or capacitive sensors physically contacting the target; or (ii) to obtain the physical or other non-mass spectrometric data by physically contacting the target with the one or more one or more dielectric property sensors or capacitive sensors.

The method may further comprise determining a dielectric property, a dielectric property profile, a capacitance or a capacitance profile of one or more regions of the target.

The step of using the physical or other non-mass spectrometric data to determine one or more regions of interest may comprise determining whether or not a region of the target has a different dielectric property or capacitance relative to normal tissue, surrounding tissue, a control sample, a control region, control data or predetermined data.

The step of using the physical or other non-mass spectrometric data to determine one or more regions of interest may comprise determining whether or not a region of the target has a higher or lower dielectric property or capacitance relative to normal tissue, surrounding tissue, a control sample, a control region, control data or predetermined data.

The method may further comprise using one or more electrochemical sensors or biosensors to obtain the physical or other non-mass spectrometric data.

The method may further comprise using the one or more electrochemical sensors or biosensor sensors either: (i) to obtain the physical or other non-mass spectrometric data without the one or more one or more electrochemical sensors or biosensors physically contacting the target; or (ii) to obtain the physical or other non-mass spectrometric data by physically contacting the target with the one or more one or more electrochemical or biosensors.

The one or more electrochemical sensors or biosensors may be embedded within the target or may be embedded within in vivo biological tissue.

The method may further comprise determining a measure of glucose, glutamate, reactive nitrogen species, insulin, dopamine (DA), serotonin (5-HT), norepinephrine (NE), nitric oxide (NO) or a neurochemical in the target.

The step of using the physical or other non-mass spectrometric data to determine one or more regions of interest may comprise determining whether or not a region of the target has a different measure of glucose, glutamate, reactive nitrogen species, insulin, dopamine (DA), serotonin (5-HT), norepinephrine (NE), nitric oxide (NO) or a neurochemical relative to normal tissue, surrounding tissue, a control sample, a control region, control data or predetermined data.

The step of using the physical or other non-mass spectrometric data to determine one or more regions of interest may comprise determining whether or not a region of the target has a higher or lower measure of glucose, glutamate, reactive nitrogen species, insulin, dopamine (DA), serotonin (5-HT), norepinephrine (NE), nitric oxide (NO) or a neurochemical relative to normal tissue, surrounding tissue, a control sample, a control region, control data or predetermined data.

The method may further comprise using the physical or other non-mass spectrometric data to determine the margins or bounds of one or more regions of interest of the target.

The method may further comprise using the physical or other non-mass spectrometric data to determine the margins or bounds of one or more regions of interest of the target.

The one or more regions of interest may comprise cancerous biological tissue or a tumour.

The cancerous biological tissue or the tumour may comprise either: (i) grade I, grade II, grade III or grade IV cancerous tissue; (ii) metastatic cancerous tissue; (iii) mixed grade cancerous tissue; or (iv) a sub-grade cancerous tissue.

The method may further comprise determining from the physical or other non-mass spectrometric data either: (i) one or more physical properties of the target; (ii) one or more chemical properties of the target; (iii) one or more physicochemical properties of the target; or (iv) one or more mechanical properties of the target.

The method may further comprise changing, controlling, varying or optimising one or more operational parameters of the first device based upon the obtained physical or other non-mass spectrometric data.

The method may further comprise using one or more contrast agents for enhancing the image data.

The one or more contrast agents may comprise one or more fluorescent contrast agents.

The one or more contrast agents may comprise one or more visible dyes.

The one or more contrast agents may comprise one or more radiocontrast agents.

The one or more contrast agents may comprise one or more optical, near infrared ("NIR"), fluorescent, autofluorescent or diagnostic contrast agents.

The one or more contrast agents may be selected from the group consisting of: (i) indocyanine green ("ICG") and derivatives or conjugates of indocyanine green including indotricarbocyanine; (ii) diethylthiatricarbocyanine iodide ("DTTCI") and derivatives or conjugates of diethylthiatricarbocyanine iodide; (iii) rhodamine B and derivatives or conjugates of rhodamine B; (iv) photodynamic therapy ("PDT") agents including hexylpyropheophorbide ("HPPH"); (v) a cyanine dye including Cy 5.5 dyes; and (vi) bifunctional contrast agents.

The one or more contrast agents may comprise nanoparticles.

The one or more contrast agents may comprise: (i) magnetic or ferromagnetic nanoparticles; (ii) gold nanoparticles; (iii) metallic nanoparticles; (iv) functionalised nanoparticles; (v) nanospheres, nanorods, nanostars or nanoshells; (vi) levan nanoparticles; or (vii) copper, zinc, titanium, magnesium, alginate, alloy or silver nanoparticles.

The one or more contrast agents may be exogenous to the target. Alternatively, the one or more contrast agents may be endogenous to the target.

According to another aspect there is provided a method of ambient ionisation comprising a method as disclosed above.

According to another aspect there is provided a method of rapid evaporation ionization mass spectrometry ("REIMS") comprising a method as disclosed above.

According to another aspect there is provided a method of analysis comprising a method as disclosed above.

According to another aspect there is provided a method of surgery, diagnosis, therapy or medical treatment comprising a method as disclosed above.

According to another aspect there is provided a non-surgical, non-therapeutic method of mass spectrometry and/or method of ion mobility analysis comprising a method as disclosed above.

According to another aspect there is provided a method of mass spectrometry and/or method of ion mobility analysis comprising a method as disclosed above.

According to another aspect there is provided apparatus comprising:

a device arranged and adapted to obtain physical or other non-mass spectrometric data from one or more regions of a target; and a first device arranged and adapted to generate aerosol, smoke or vapour from one or more regions of the target.

The apparatus may further comprise a control system arranged and adapted to use the physical or other non-mass spectrometric data to determine one or more regions of interest of the target.

The physical or other non-mass spectrometric data may comprise data selected from the group consisting of: (i) density data; (ii) impedance data; (iii) hardness data; (iv) surface hardness data; (v) tissue hardness data; (vi) tactile data; (vii) force data; (viii) radio-frequency absorbance data; (ix) microwave reflectance or transmission data; (x) dielectric property data; (xi) dielectric permittivity or conductivity data; (xxii) Young's modulus data; and (xxiii) capacitance or resistance data.

The first device may comprise or form part of an ambient ion or ionisation source or the first device may generate the aerosol, smoke or vapour for subsequent ionisation by an ambient ion or ionisation source or other ionisation source.

The target may comprise native or unmodified target material.

The native or unmodified target material may be unmodified by the addition of a matrix or reagent.

The first device may be arranged and adapted to generate aerosol, smoke or vapour from one or more regions of the target without the target requiring prior preparation.

The first device may comprise an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a focussed or unfocussed ultrasonic ablation device; (xxii) a microwave resonance device; and (xxiii) a pulsed plasma RF dissection device.

The first device may be arranged and adapted to generate aerosol, smoke or vapour from one or more regions of the target by contacting the target with one or more electrodes.

The one or more electrodes may comprise a bipolar device or a monopolar device.

The one or more electrodes may comprise: (i) a monopolar device, wherein the apparatus optionally further comprises a separate return electrode; (ii) a bipolar device; or (iii) a multi phase RF device, wherein the apparatus optionally further comprises a separate return electrode or electrodes.

The one or more electrodes may comprise a rapid evaporation ionization mass spectrometry ("REIMS") device.

The apparatus may further comprise a device arranged and adapted to apply an AC or RF voltage to the one or more electrodes in order to generate the aerosol, smoke or vapour.

The device for applying the AC or RF voltage to the one or more electrodes may be arranged to apply one or more pulses of the AC or RF voltage to the one or more electrodes.

Application of the AC or RF voltage to the one or more electrodes may cause heat to be dissipated into the target.

The first device may comprise a laser for irradiating the target.

The first device may be arranged and adapted to generate aerosol from one or more regions of the target by direct evaporation or vaporisation of target material from the target by Joule heating or diathermy.

The first device may be arranged and adapted to direct ultrasonic energy into the target.

The aerosol may comprise uncharged aqueous droplets optionally comprising cellular material.

At least 50%, 55%, 60%, 65%, 70%, 75%, 80%, 85%, 90% or 95% of the mass or matter generated by the first device and which forms the aerosol may be in the form of droplets.

The first device may be arranged and adapted to generate aerosol wherein the Sauter mean diameter ("SMD", d32) of the aerosol may be in a range: (i) <5 µm; (ii) 5-10 µm; (iii) 10-15 µm; (iv) 15-20 µm; (v) 20-25 µm; or (vi) >25 µm.

The aerosol may traverse a flow region with a Reynolds number (Re) in the range: (i) <2000; (ii) 2000-2500; (iii) 2500-3000; (iv) 3000-3500; (v) 3500-4000; or (vi) >4000.

Substantially at the point of generating the aerosol, the aerosol may comprise droplets having a Weber number (We) selected from the group consisting of: (i) <50; (ii) 50-100; (iii) 100-150; (iv) 150-200; (v) 200-250(vi) 250-300; (vii) 300-350; (viii) 350-400; (ix) 400-450; (x) 450-500; (xi) 500-550; (xii) 550-600; (xiii) 600-650; (xiv) 650-700; (xv) 700-750; (xvi) 750-800; (xvii) 800-850; (xviii) 850-900; (xix) 900-950; (xx)$_{950}$-1000; and (xxi) >1000.

Substantially at the point of generating the aerosol, the aerosol may comprise droplets having a Stokes number ($S_k$) in the range: (i) 1-5; (ii) 5-10; (iii) 10-15; (iv) 15-20; (v) 20-25; (vi) 25-30; (vii) 30-35; (viii) 35-40; (ix) 40-45; (x) 45-50; and (xi) >50.

Substantially at the point of generating the aerosol, the aerosol may comprise droplets having a mean axial velocity selected from the group consisting of: (i) <20 m/s; (ii) 20-30 m/s; (iii) 30-40 m/s; (iv) 40-50 m/s; (v) 50-60 m/s; (vi) 60-70 m/s; (vii) 70-80 m/s; (viii) 80-90 m/s; (ix) 90-100 m/s; (x) 100-110 m/s; (xi) 110-120 m/s; (xii) 120-130 m/s; (xiii) 130-140 m/s; (xiv) 140-150 m/s; and (xv) >150 m/s.

The target may comprise biological tissue.

The biological tissue may comprise human tissue or non-human animal tissue.

The biological tissue may comprise in vivo biological tissue.

The biological tissue may comprise ex vivo biological tissue.

The biological tissue may comprise in vitro biological tissue.

The biological tissue may comprise: (i) adrenal gland tissue, appendix tissue, bladder tissue, bone, bowel tissue, brain tissue, breast tissue, bronchi, coronal tissue, ear tissue, esophagus tissue, eye tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, ureter tissue, urethra tissue, soft and connective tissue, peritoneal tissue, blood vessel tissue and/or fat tissue; (ii) grade I, grade II, grade III or grade IV cancerous tissue; (iii) metastatic cancerous tissue; (iv) mixed grade cancerous tissue; (v) a sub-grade cancerous tissue; (vi) healthy or normal tissue; or (vii) cancerous or abnormal tissue.

The first device may comprise a point of care ("POC"), diagnostic or surgical device.

The apparatus may further comprise an ion source for ionising at least some of the aerosol, smoke or vapour so as to generate analyte ions.

The apparatus may further comprise a device for directing or aspirating at least some of the aerosol, smoke or vapour into a vacuum chamber of a mass spectrometer and/or ion mobility spectrometer.

The apparatus may further comprise a device for ionising at least some the aerosol, smoke or vapour within a or the vacuum chamber of the mass spectrometer and/or ion mobility spectrometer so as to generate a plurality of analyte ions.

The apparatus may further comprise device for directing the aerosol, smoke or vapour to impact upon a collision surface located within a vacuum chamber of the mass spectrometer and/or ion mobility spectrometer so as to generate a plurality of analyte ions.

The apparatus may further comprise a mass analyser for mass analysing the analyte ions and/or an ion mobility analyser for ion mobility analysing the analyte ions in order to obtain mass spectrometric data and/or ion mobility data.

The apparatus may further comprise a mass analyser and/or ion mobility analyser for mass analysing and/or ion mobility analysing the aerosol, smoke or vapour or ions derived from the aerosol, smoke or vapour in order to obtain mass spectrometric data and/or ion mobility data.

The apparatus may further comprise a control system arranged and adapted to analyse the mass spectrometric data and/or ion mobility data in order either: (i) to distinguish between healthy and diseased tissue; (ii) to distinguish between potentially cancerous and non-cancerous tissue; (iii) to distinguish between different types or grades of cancerous tissue; (iv) to distinguish between different types or classes of target material; (v) to determine whether or not one or more desired or undesired substances may be present in the target; (vi) to confirm the identity or authenticity of the target; (vii) to determine whether or not one or more impurities, illegal substances or undesired substances may be present in the target; (viii) to determine whether a human or animal patient may be at an increased risk of suffering an adverse outcome; (ix) to make or assist in the making a diagnosis or prognosis; and (x) to inform a surgeon, nurse, medic or robot of a medical, surgical or diagnostic outcome.

The control system may be arranged and adapted to perform a supervised or unsupervised multivariate statistical analysis of the mass spectrometric data.

According to an embodiment either: (i) the multivariate statistical analysis may comprise principal component analysis ("PCA"); (ii) the multivariate statistical analysis may comprise linear discriminant analysis ("LDA"); (iii) the multivariate statistical analysis may be performed by a neural network; (iv) the multivariate statistical analysis may be performed by a support vector machine; or (v) the multivariate statistical analysis may comprise subspace discriminant analysis.

The apparatus may further comprise a control system arranged and adapted to analyse a profile of the aerosol, smoke or vapour or a profile of ions derived from the aerosol, smoke or vapour.

The profile may be selected from the group consisting of: (i) a lipidomic profile; (ii) a fatty acid profile; (iii) a phospholipid profile; (iv) a phosphatidic acid (PA) profile; (v) a phosphatidylethanolamine (PE) profile; (vi) a phosphatidylglycerol (PG) profile; (vii) a phosphatidylserines (PS) profile; (viii) a phosphatidylinositol (PI) profile; or (ix) a triglyceride (TG) profile.

The apparatus may further comprise one or more impedance sensors for obtaining the physical or other non-mass spectrometric data.

The apparatus may further comprise one or more impedance sensors may be arranged and adapted either: (i) to obtain the physical or other non-mass spectrometric data without the one or more impedance sensors physically contacting the target; or (ii) to obtain the physical or other non-mass spectrometric data by physically contacting the target with the one or more impedance sensors.

The apparatus may further comprise a control system arranged and adapted to determine a density, a density profile, an impedance or an impedance profile of one or more regions of the target.

The control system may be arranged and adapted to determine one or more regions of the target which have a different density or impedance relative to normal tissue, surrounding tissue, a control sample, a control region, control data or predetermined data.

The control system may be arranged and adapted to determine whether or not a region of the target has a higher or lower density or impedance relative to normal tissue, surrounding tissue, a control sample, a control region, control data or predetermined data.

The apparatus may further comprise one or more force or tactile sensors for obtaining the physical or other non-mass spectrometric data.

The one or more force or tactile sensors may be arranged and adapted to obtain the physical or other non-mass spectrometric data by physically contacting the target with the one or more force or tactile sensors.

The apparatus may further comprise a control system arranged and adapted to determine a density, a density profile, a force, a force profile, a surface hardness or a surface hardness profile of one or more regions of the target.

The control system may be arranged and adapted to determine one or more regions of interest by determining one or more regions of the target which have a different density or surface hardness relative to normal tissue, surrounding tissue, a control sample, a control region, control data or predetermined data.

The control system may be arranged and adapted to determine whether or not a region of the target has a higher or lower density or surface hardness relative to normal tissue, surrounding tissue, a control sample, a control region, control data or predetermined data.

The apparatus may further comprise one or more radio-frequency ("RF") or microwave sensors for obtaining the physical or other non-mass spectrometric data.

The one or more radio-frequency ("RF") or microwave sensors may be arranged and adapted either: (i) to obtain the physical or other non-mass spectrometric data without the one or more one or more radio-frequency ("RF") or microwave sensors physically contacting the target; or (ii) to obtain the physical or other non-mass spectrometric data by physically contacting the target with the one or more one or more radio-frequency ("RF") or microwave sensors.

The apparatus may further comprise a control system arranged and adapted to determine a density, a density profile, a radio-frequency absorbance, a radio-frequency absorbance profile, a microwave reflectance or transmission, a microwave reflectance or transmission profile, a dielectric property, a dielectric property profile, a dielectric permittivity, a dielectric permittivity profile, a conductivity or a conductivity profile of one or more regions of the target.

The control system may be arranged and adapted to determine whether a region of the target has a different density, radio-frequency absorbance, microwave reflectance or transmission, dielectric property, permittivity or conductivity relative to normal tissue, surrounding tissue, a control sample, a control region, control data or predetermined data.

The control system may be arranged and adapted to determine whether or not a region of the target has a higher or lower density, radio-frequency absorbance, microwave reflectance or transmission, dielectric property, permittivity or conductivity relative to normal tissue, surrounding tissue, a control sample, a control region, control data or predetermined data.

The apparatus may further comprise one or more dielectric property sensors or capacitive sensors for obtaining the physical or other non-mass spectrometric data.

The one or more dielectric property sensors or capacitive sensors may be arranged and adapted either: (i) to obtain the physical or other non-mass spectrometric data without the one or more one or more dielectric property sensors or capacitive sensors physically contacting the target; or (ii) to obtain the physical or other non-mass spectrometric data by physically contacting the target with the one or more one or more dielectric property sensors or capacitive sensors.

The apparatus may further comprise a control system arranged and adapted to determine a dielectric property, a dielectric property profile, a capacitance or a capacitance profile of one or more regions of the target.

The control system may be arranged and adapted to determine whether or not a region of the target has a different dielectric property or capacitance relative to normal tissue, surrounding tissue, a control sample, a control region, control data or predetermined data.

The control system may be arranged and adapted to determine whether or not a region of the target has a higher or lower dielectric property or capacitance relative to normal tissue, surrounding tissue, a control sample, a control region, control data or predetermined data.

The apparatus may further comprise one or more electrochemical sensors or biosensors for obtaining the physical or other non-mass spectrometric data.

The one or more electrochemical sensors or biosensor sensors may be arranged and adapted either: (i) to obtain the physical or other non-mass spectrometric data without the one or more one or more electrochemical sensors or biosensors physically contacting the target; or (ii) to obtain the physical or other non-mass spectrometric data by physically contacting the target with the one or more one or more electrochemical or biosensors.

The one or more electrochemical sensors or biosensors may be embedded within the target or may be embedded within in vivo biological tissue.

The apparatus may further comprise a device arranged and adapted to determine a measure of glucose, glutamate, reactive nitrogen species, insulin, dopamine (DA), serotonin (5-HT), norepinephrine (NE), nitric oxide (NO) or a neurochemical in the target.

The apparatus may further comprise a control system arranged and adapted to determine whether or not a region of the target has a different measure of glucose, glutamate, reactive nitrogen species, insulin, dopamine (DA), serotonin (5-HT), norepinephrine (NE), nitric oxide (NO) or a neurochemical relative to normal tissue, surrounding tissue, a control sample, a control region, control data or predetermined data.

The control system may be arranged and adapted to determine whether or not a region of the target has a higher or lower measure of glucose, glutamate, reactive nitrogen species, insulin, dopamine (DA), serotonin (5-HT), norepinephrine (NE), nitric oxide (NO) or a neurochemical relative to normal tissue, surrounding tissue, a control sample, a control region, control data or predetermined data.

The apparatus may further comprise a control system arranged and adapted to use the physical or other non-mass spectrometric data to determine the margins or bounds of one or more regions of interest of the target.

The apparatus may further comprise a control system arranged and adapted to use the physical or other non-mass spectrometric data to determine the margins or bounds of one or more regions of interest of the target.

The one or more regions of interest may comprise cancerous biological tissue or a tumour.

The cancerous biological tissue or the tumour may comprise either: (i) grade I, grade II, grade III or grade IV cancerous tissue; (ii) metastatic cancerous tissue; (iii) mixed grade cancerous tissue; or (iv) a sub-grade cancerous tissue.

The apparatus may further comprise a control system arranged and adapted to determine from the physical or other non-mass spectrometric data either: (i) one or more physical properties of the target; (ii) one or more chemical properties of the target; (iii) one or more physico-chemical properties of the target; or (iv) one or more mechanical properties of the target.

The apparatus may further comprise a control system arranged and adapted to change, control, vary or optimise one or more operational parameters of the first device based upon the obtained physical or other non-mass spectrometric data.

The apparatus may further comprise one or more contrast agents for enhancing the image data.

The one or more contrast agents may comprise one or more fluorescent contrast agents.

The one or more contrast agents may comprise one or more visible dyes.

The one or more contrast agents may comprise one or more radiocontrast agents.

The one or more contrast agents may comprise one or more optical, near infrared ("NIR"), fluorescent, autofluorescent or diagnostic contrast agents.

The one or more contrast agents may be selected from the group consisting of: (i) indocyanine green ("ICG") and derivatives or conjugates of indocyanine green including indotricarbocyanine; (ii) diethylthiatricarbocyanine iodide ("DTTCI") and derivatives or conjugates of diethylthiatricarbocyanine iodide; (iii) rhodamine B and derivatives or conjugates of rhodamine B; (iv) photodynamic therapy ("PDT") agents including hexylpyropheophorbide ("HPPH"); (v) a cyanine dye including Cy 5.5 dyes; and (vi) bifunctional contrast agents.

The one or more contrast agents may comprise nanoparticles.

The one or more contrast agents may comprise: (i) magnetic or ferromagnetic nanoparticles; (ii) gold nanoparticles; (iii) metallic nanoparticles; (iv) functionalised nanoparticles; (v) nanospheres, nanorods, nanostars or nanoshells; (vi) levan nanoparticles; or (vii) copper, zinc, titanium, magnesium, alginate, alloy or silver nanoparticles.

The one or more contrast agents may be exogenous to the target. Alternatively, the one or more contrast agents may be endogenous to the target.

According to another aspect there is provided an ambient ionisation ion source comprising apparatus as disclosed above.

According to another aspect there is provided a rapid evaporation ionization mass spectrometry ("REIMS") ion source comprising apparatus as disclosed above.

According to another aspect there is provided analysis apparatus comprising apparatus as disclosed above.

According to another aspect there is provided a mass spectrometer and/or ion mobility analyser comprising apparatus as disclosed above.

Various embodiments are contemplated which relate to generating smoke, aerosol or vapour from a target (details of which are provided elsewhere herein) using an ambient ionisation ion source. The aerosol, smoke or vapour may then be mixed with a matrix and aspirated into a vacuum chamber of a mass spectrometer and/or ion mobility spectrometer. The mixture may be caused to impact upon a collision surface causing the aerosol, smoke or vapour to be ionised by impact ionization which results in the generation of analyte ions. The resulting analyte ions (or fragment or product ions derived from the analyte ions) may then be mass analysed and/or ion mobility analysed and the resulting mass spectrometric data and/or ion mobility spectrometric data may be subjected to multivariate analysis or other mathematical treatment in order to determine one or more properties of the target in real time.

According to an embodiment the first device for generating aerosol, smoke or vapour from the target may comprise a tool which utilises an RF voltage, such as a continuous RF waveform.

Other embodiments are contemplated wherein the first device for generating aerosol, smoke or vapour from the target may comprise an argon plasma coagulation ("APC") device. An argon plasma coagulation device involves the use of a jet of ionised argon gas (plasma) that is directed through a probe. The probe may be passed through an endoscope. Argon plasma coagulation is essentially a non-contact process as the probe is placed at some distance from the target. Argon gas is emitted from the probe and is then ionized by a high voltage discharge (e.g., 6 kV). High-frequency electric current is then conducted through the jet of gas, resulting in coagulation of the target on the other end of the jet. The depth of coagulation is usually only a few millimetres.

The first device, surgical or electrosurgical tool, device or probe or other sampling device or probe disclosed in any of the aspects or embodiments herein may comprise a non-contact surgical device, such as one or more of a hydrosurgical device, a surgical water jet device, an argon plasma coagulation device, a hybrid argon plasma coagulation device, a water jet device and a laser device.

A non-contact surgical device may be defined as a surgical device arranged and adapted to dissect, fragment, liquefy, aspirate, fulgurate or otherwise disrupt biologic tissue without physically contacting the tissue. Examples include laser devices, hydrosurgical devices, argon plasma coagulation devices and hybrid argon plasma coagulation devices.

As the non-contact device may not make physical contact with the tissue, the procedure may be seen as relatively safe and can be used to treat delicate tissue having low intracellular bonds, such as skin or fat.

According to various embodiments the mass spectrometer and/or ion mobility spectrometer may obtain data in negative ion mode only, positive ion mode only, or in both positive and negative ion modes. Positive ion mode spectrometric data may be combined or concatenated with negative ion mode spectrometric data. Negative ion mode can provide particularly useful spectra for classifying aerosol, smoke or vapour samples, such as aerosol, smoke or vapour samples from targets comprising lipids.

Ion mobility spectrometric data may be obtained using different ion mobility drift gases, or dopants may be added to the drift gas to induce a change in drift time of one or more species. This data may then be combined or concatenated.

It will be apparent that the requirement to add a matrix or a reagent directly to a sample may prevent the ability to perform in vivo analysis of tissue and also, more generally, prevents the ability to provide a rapid simple analysis of target material.

According to other embodiments the ambient ionisation ion source may comprise an ultrasonic ablation ion source or a hybrid electrosurgical-ultrasonic ablation source that generates a liquid sample which is then aspirated as an aerosol. The ultrasonic ablation ion source may comprise a focused or unfocussed ultrasound.

Optionally, the first device comprises or forms part of an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a hybrid CUSA-diathermy device; (xxii) a focussed or unfocussed ultrasonic ablation device; (xxiii) a hybrid focussed or unfocussed ultrasonic ablation and diathermy device; (xxiv) a microwave resonance device; (xxv) a pulsed plasma RF dissection device; (xxvi) an argon plasma coagulation device; (xxvi) a hybrid pulsed plasma RF dissection and argon plasma coagulation device; (xxvii) a hybrid pulsed plasma RF dissection and JeDI device; (xxviii) a surgical water/saline jet device; (xxix) a hybrid electrosurgery and argon plasma coagulation device; and (xxx) a hybrid argon plasma coagulation and water/saline jet device.

BRIEF DESCRIPTION OF THE DRAWINGS

Various embodiments will now be described, by way of example only, and with reference to the accompanying drawings in which.

DETAILED DESCRIPTION

Figure 1:
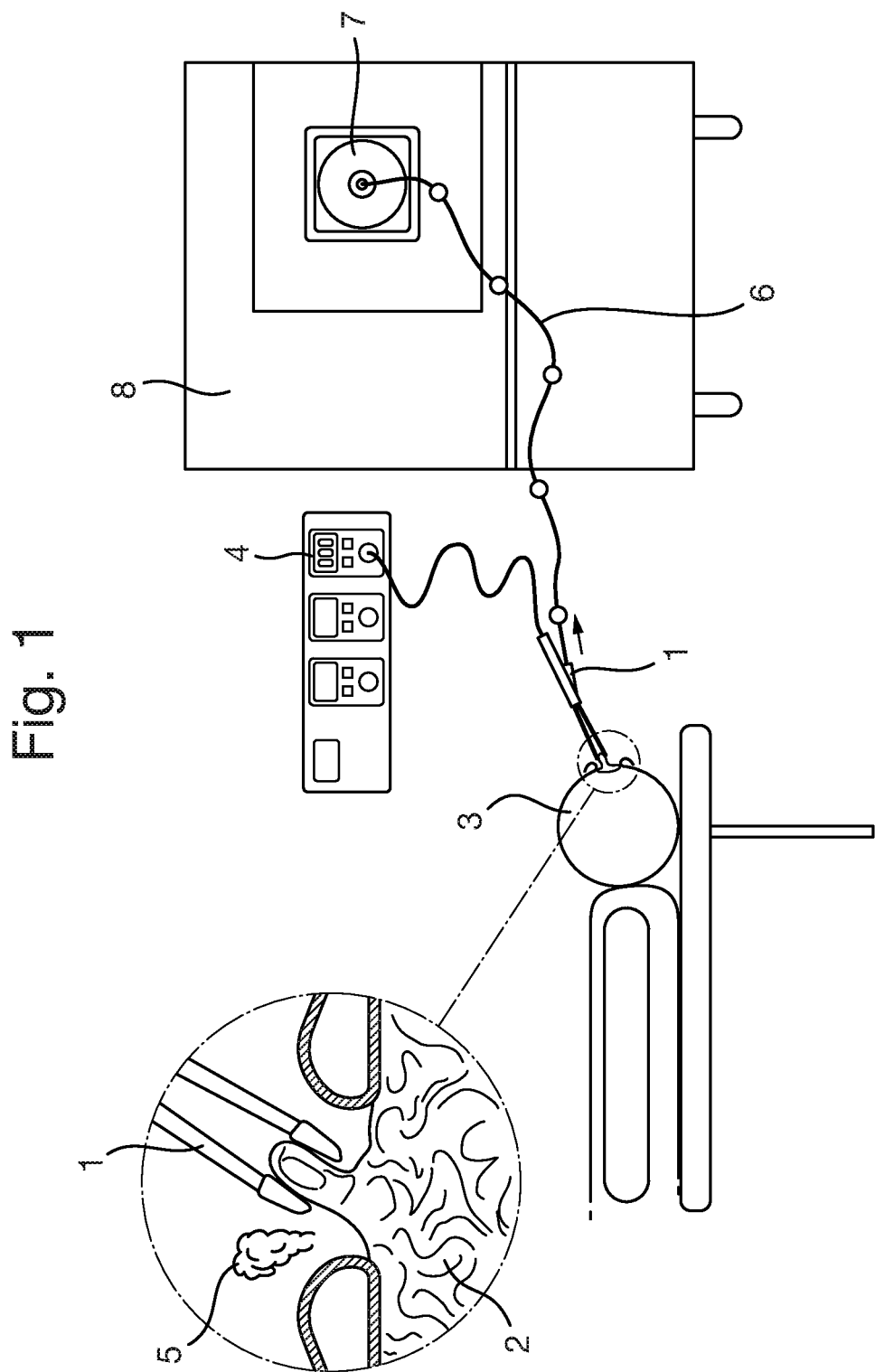
FIG. 1 illustrates a method of rapid evaporative ionisation mass spectrometry ("REIMS") wherein an RF voltage is applied to bipolar forceps resulting in the generation of an aerosol or surgical plume which is then captured through an irrigation port of the bipolar forceps and is then transferred to a mass spectrometer for mass analysis.

Various embodiments will now be described in more detail below which in general relate to obtaining physical non-mass spectrometric data or other non-mass spectrometric data from one or more regions of a target (e.g., in vivo tissue) and then generating an aerosol, surgical smoke or vapour from one or more regions of the target using an ambient ionisation ion source.

The aerosol, surgical smoke or vapour is then aspirated into a vacuum chamber of a mass spectrometer and/or ion mobility spectrometer and is caused to impact upon a collision surface causing the aerosol, smoke or vapour to be ionised by impact ionisation which results in the generation of analyte ions.

The resulting analyte ions (or fragment or product ions derived from the analyte ions) are then mass analysed and/or ion mobility analysed and the resulting mass spectrometric data and/or ion mobility data may then be subjected to multivariate analysis in order to determine one or more properties of the target in real time.

For example, the multivariate analysis may enable a determination to be made as to whether or not a portion of tissue which is currently being resected is cancerous or not.

The use of physical data enables tissue which is of potential concern to be identified either prior to and/or during a surgical procedure and enables a surgeon to have a greater confidence that all undesired or potentially cancerous tissue is both located and completely removed whilst at the same time ensuring that the minimum amount of healthy tissue is removed.

Ambient Ionisation Ion Sources

According to various embodiments a device is used to generate an aerosol, smoke or vapour from one or more regions of a target (e.g., in vivo tissue). The device may comprise an ambient ionisation ion source which is characterised by the ability to generate analyte aerosol, smoke or vapour from a native or unmodified target. For example, other types of ionisation ion sources such as Matrix Assisted Laser Desorption Ionisation ("MALDI") ion sources require a matrix or reagent to be added to the sample prior to ionisation.

It will be apparent that the requirement to add a matrix or a reagent to a sample prevents the ability to perform in vivo analysis of tissue and also, more generally, prevents the ability to provide a rapid simple analysis of target material.

In contrast, therefore, ambient ionisation techniques are particularly advantageous since firstly they do not require the addition of a matrix or a reagent (and hence are suitable for the analysis of in vivo tissue) and since secondly they enable a rapid simple analysis of target material to be performed.

A number of different ambient ionisation techniques are known and are intended to fall within the scope of the present invention. As a matter of historical record, Desorption Electrospray Ionisation ("DESI") was the first ambient ionisation technique to be developed and was disclosed in 2004. Since 2004, a number of other ambient ionisation techniques have been developed. These ambient ionisation techniques differ in their precise ionisation method but they share the same general capability of generating gas-phase ions directly from native (i.e. untreated or unmodified) samples. A particular advantage of the various ambient ionisation techniques which are intended to fall within the scope of the present invention is that the various ambient ionisation techniques do not require any prior sample preparation. As a result, the various ambient ionisation techniques enable both in vivo tissue and ex vivo tissue samples to be analysed without necessitating the time and expense of adding a matrix or reagent to the tissue sample or other target material.

A list of ambient ionisation techniques which are intended to fall within the scope of the present invention are given in the following table:

| Acronym | Ionisation technique |
| --- | --- |
| DESI | Desorption electrospray ionisation |
| DeSSI | Desorption sonic spray ionisation |
| DAPPI | Desorption atmospheric pressure photoionization |

-continued

| Acronym | Ionisation technique |
| --- | --- |
| EASI | Easy ambient sonic-spray ionization |
| JeDI | Jet desorption electrospray ionization |
| TM-DESI | Transmission mode desorption electrospray ionization |
| LMJ-SSP | Liquid microjunction-surface sampling probe |
| DICE | Desorption ionization by charge exchange |
| Nano-DESI | Nanospray desorption electrospray ionization |
| EADESI | Electrode-assisted desorption electrospray ionization |
| APTDCI | Atmospheric pressure thermal desorption chemical ionization |
| V-EASI | Venturi easy ambient sonic-spray ionization |
| AFAI | Air flow-assisted ionization |
| LESA | Liquid extraction surface analysis |
| PTC-ESI | Pipette tip column electrospray ionization |
| AFADESI | Air flow-assisted desorption electrospray ionization |
| DEFFI | Desorption electro-flow focusing ionization |
| ESTASI | Electrostatic spray ionization |
| PASIT | Plasma-based ambient sampling ionization transmission |
| DAPCI | Desorption atmospheric pressure chemical ionization |
| DART | Direct analysis in real time |
| ASAP | Atmospheric pressure solid analysis probe |
| APTDI | Atmospheric pressure thermal desorption ionization |
| PADI | Plasma assisted desorption ionization |
| DBDI | Dielectric barrier discharge ionization |
| FAPA | Flowing atmospheric pressure afterglow |
| HAPGDI | Helium atmospheric pressure glow discharge ionization |
| APGDDI | Atmospheric pressure glow discharge desorption ionization |
| LTP | Low temperature plasma |
| LS-APGD | Liquid sampling-atmospheric pressure glow discharge |
| MIPDI | Microwave induced plasma desorption ionization |
| MFGDP | Microfabricated glow discharge plasma |
| RoPPI | Robotic plasma probe ionization |
| PLASI | Plasma spray ionization |
| MALDESI | Matrix assisted laser desorption electrospray ionization |
| ELDI | Electrospray laser desorption ionization |
| LDTD | Laser diode thermal desorption |
| LAESI | Laser ablation electrospray ionization |
| CALDI | Charge assisted laser desorption ionization |
| LA-FAPA | Laser ablation flowing atmospheric pressure afterglow |
| LADESI | Laser assisted desorption electrospray ionization |
| LDESI | Laser desorption electrospray ionization |
| LEMS | Laser electrospray mass spectrometry |
| LSI | Laser spray ionization |
| IR-LAMICI | Infrared laser ablation metastable induced chemical ionization |
| LDSPI | Laser desorption spray post-ionization |
| PAMLDI | Plasma assisted multiwavelength laser desorption ionization |
| HALDI | High voltage-assisted laser desorption ionization |
| PALDI | Plasma assisted laser desorption ionization |
| ESSI | Extractive electrospray ionization |
| PESI | Probe electrospray ionization |
| ND-ESSI | Neutral desorption extractive electrospray ionization |
| PS | Paper spray |
| DIP-APCI | Direct inlet probe-atmospheric pressure chemical ionization |
| TS | Touch spray |
| Wooden-tip | Wooden-tip electrospray |
| CBS-SPME | Coated blade spray solid phase microextraction |
| TSI | Tissue spray ionization |
| RADIO | Radiofrequency acoustic desorption ionization |

-continued

| Acronym | Ionisation technique |
|---|---|
| LIAD-ESI | Laser induced acoustic desorption electrospray ionization |
| SAWN | Surface acoustic wave nebulization |
| UASI | Ultrasonication-assisted spray ionization |
| SPA-nanoESI | Solid probe assisted nanoelectrospray ionization |
| PAUSI | Paper assisted ultrasonic spray ionization |
| DPESI | Direct probe electrospray ionization |
| ESA-Py | Electrospray assisted pyrolysis ionization |
| APPIS | Ambient pressure pyroelectric ion source |
| RASTIR | Remote analyte sampling transport and ionization relay |
| SACI | Surface activated chemical ionization |
| DEMI | Desorption electrospray metastable-induced ionization |
| REIMS | Rapid evaporative ionization mass spectrometry |
| SPAM | Single particle aerosol mass spectrometry |
| TDAMS | Thermal desorption-based ambient mass spectrometry |
| MAII | Matrix assisted inlet ionization |
| SAII | Solvent assisted inlet ionization |
| SwiFERR | Switched ferroelectric plasma ionizer |
| LPTD | Leidenfrost phenomenon assisted thermal desorption |

According to an embodiment the ambient ionisation ion source may comprise a rapid evaporative ionisation mass spectrometry ("REIMS") ion source wherein a RF voltage is applied to one or more electrodes in order to generate an aerosol or plume of surgical smoke by Joule heating.

However, it will be appreciated that other ambient ion sources including those referred to above may also be utilised. For example, according to another embodiment the ambient ionisation ion source may comprise a laser ionisation ion source. According to an embodiment the laser ionisation ion source may comprise a mid-IR laser ablation ion source. For example, there are several lasers which emit radiation close to or at 2.94 µm which corresponds with the peak in the water absorption spectrum. According to various embodiments the ambient ionisation ion source may comprise a laser ablation ion source having a wavelength close to 2.94 µm on the basis of the high absorption coefficient of water at 2.94 µm. According to an embodiment the laser ablation ion source may comprise a Er:YAG laser which emits radiation at 2.94 µm.

Other embodiments are contemplated wherein a mid-infrared optical parametric oscillator ("OPO") may be used to produce a laser ablation ion source having a longer wavelength than 2.94 µm. For example, an Er:YAG pumped ZGP-OPO may be used to produce laser radiation having a wavelength of e.g. 6.1 µm, 6.45 µm or 6.73 µm. In some situations it may be advantageous to use a laser ablation ion source having a shorter or longer wavelength than 2.94 µm since only the surface layers will be ablated and less thermal damage may result. According to an embodiment a Co:MgF$_2$ laser may be used as a laser ablation ion source wherein the laser may be tuned from 1.75-2.5 µm. According to another embodiment an optical parametric oscillator ("OPO") system pumped by a Nd:YAG laser may be used to produce a laser ablation ion source having a wavelength between 2.9-3.1 µm. According to another embodiment a CO$_2$ laser having a wavelength of 10.6 µm may be used to generate the aerosol, smoke or vapour.

According to other embodiments the ambient ionisation ion source may comprise an ultrasonic ablation ion source which generates a liquid sample which is then aspirated as an aerosol. The ultrasonic ablation ion source may comprise a focused or unfocussed source.

According to an embodiment the first device for generating aerosol, smoke or vapour from one or more regions of a target may comprise an electrosurgical tool which utilises a continuous RF waveform. According to other embodiments a radiofrequency tissue dissection system may be used which is arranged to supply pulsed plasma RF energy to a tool. The tool may comprise, for example, a PlasmaBlade (®). Pulsed plasma RF tools operate at lower temperatures than conventional electrosurgical tools (e.g. 40-170° C. c.f. 200-350° C.) thereby reducing thermal injury depth. Pulsed waveforms and duty cycles may be used for both cut and coagulation modes of operation by inducing electrical plasma along the cutting edge(s) of a thin insulated electrode.

Rapid Evaporative Ionisation Mass Spectrometry ("REIMS")

FIG. 1 illustrates a method of rapid evaporative ionisation mass spectrometry ("REIMS") wherein bipolar forceps 1 may be brought into contact with in vivo tissue 2 of a patient 3. In the example shown in FIG. 1, the bipolar forceps 1 may be brought into contact with brain tissue 2 of a patient 3 during the course of a surgical operation on the patient's brain. An RF voltage from an RF voltage generator 4 may be applied to the bipolar forceps 1 which causes localised Joule or diathermy heating of the tissue 2. As a result, an aerosol or surgical plume 5 is generated. The aerosol or surgical plume 5 may then be captured or otherwise aspirated through an irrigation port of the bipolar forceps 1. The irrigation port of the bipolar forceps 1 is therefore reutilised as an aspiration port. The aerosol or surgical plume 5 may then be passed from the irrigation (aspiration) port of the bipolar forceps 1 to tubing 6 (e.g. ⅛" or 3.2 mm diameter Teflon (RTM) tubing). The tubing 6 is arranged to transfer the aerosol or surgical plume 5 to an atmospheric pressure interface 7 of a mass spectrometer and/or ion mobility spectrometer 8.

According to various embodiments a matrix comprising an organic solvent such as isopropanol may be added to the aerosol or surgical plume 5 at the atmospheric pressure interface 7. The mixture of aerosol 3 and organic solvent may then be arranged to impact upon a collision surface within a vacuum chamber of the mass spectrometer and/or ion mobility spectrometer 8. According to one embodiment the collision surface may be heated. The aerosol is caused to ionise upon impacting the collision surface resulting in the generation of analyte ions. The ionisation efficiency of generating the analyte ions may be improved by the addition of the organic solvent. However, the addition of an organic solvent is not essential.

Analyte ions which are generated by causing the aerosol, smoke or vapour 5 to impact upon the collision surface are then passed through subsequent stages of the mass spectrometer and/or ion mobility spectrometer and are subjected to mass analysis and/or ion mobility analysis in a mass analyser and/or ion mobility analyser. The mass analyser may, for example, comprise a quadrupole mass analyser or a Time of Flight mass analyser.

Figure 2:
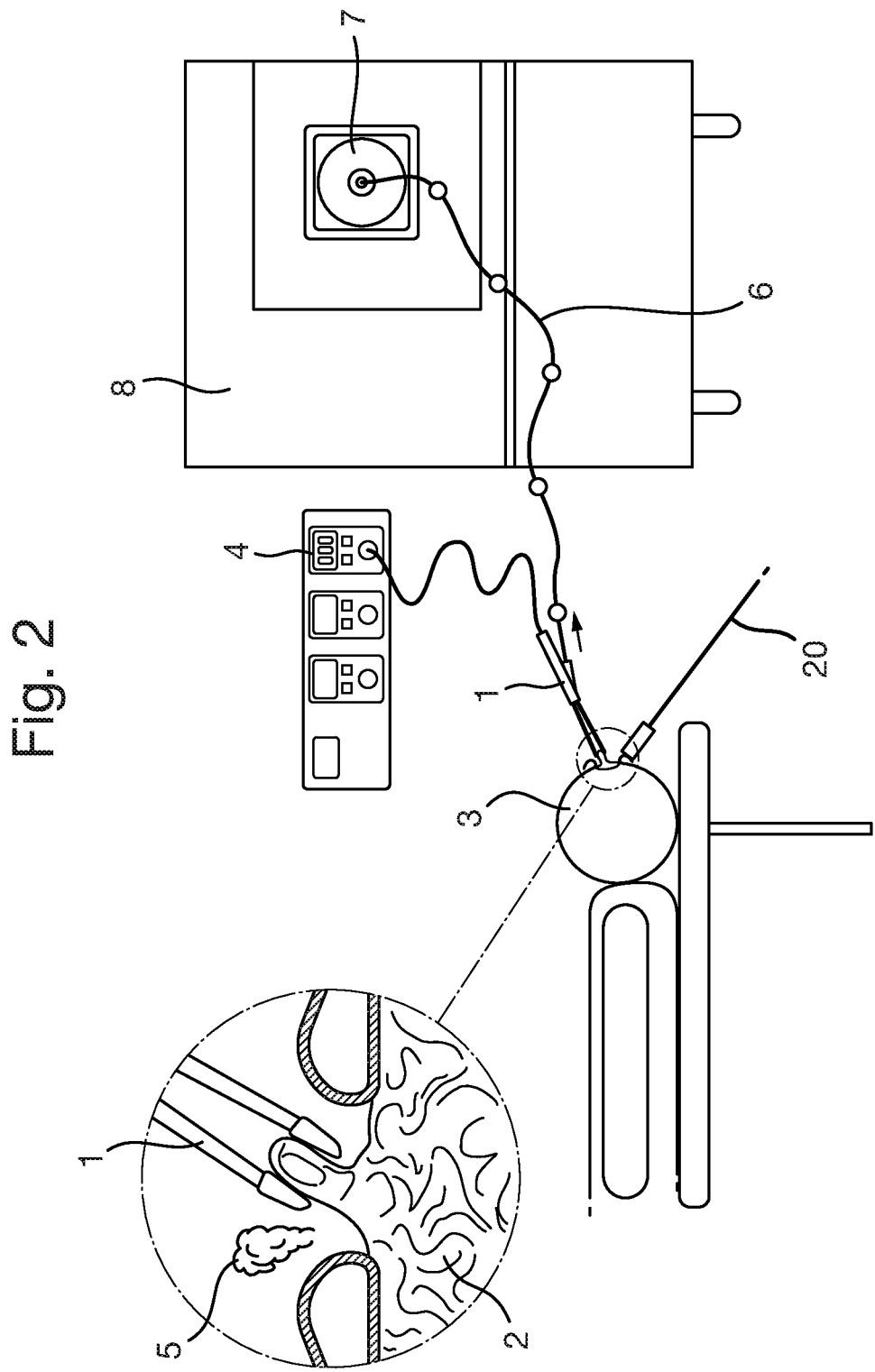
FIG. 2 illustrates a general embodiment wherein one or more physical sensors are used to obtain physical data from a target (e.g. in vivo tissue) prior to activating a rapid evaporative ionisation mass spectrometry ("REIMS") ion source to inter alia analyse the target and to determine, for example, whether or not the tissue is cancerous.

FIG. 2 illustrates a general embodiment wherein one or more physical sensors 20 are used to obtain physical non-mass spectrometric data from a target 2 (e.g. in vivo tissue) prior to activating a rapid evaporative ionisation mass spectrometry ("REIMS") ion source 1 which inter alia samples tissue 2 and enables a determination to be made, for example, as to whether or not the issue is cancerous.

According to various embodiments the one or more physical sensor devices 20 may be used to obtain physical (or other closely related) non-mass spectrometric data from the target (e.g. either in vivo or ex vivo biological tissue). The one or more physical sensor devices 20 may be arranged, for example, to obtain from the target: (i) density data; (ii) impedance data; (iii) hardness data; (iv) surface hardness data; (v) tissue hardness data; (vi) tactile data; (vii) force data; (viii) radio-frequency absorbance data; (ix) microwave reflectance or transmission data; (x) dielectric property data; (xi) dielectric permittivity or conductivity data; (xxii) Young's modulus data; or (xxiii) capacitance or resistance data.

A number of different embodiments are contemplated and will be described in more detail below wherein physical (or other closely related) data is acquired using one or more physical sensors or devices 20 and wherein the physical data may then be used, for example, to guide a user (e.g. a surgeon) performing a surgical, diagnostic or other procedure utilising an ambient ionisation ion source to one or more regions of particular interest on a target (e.g. in vivo or ex vivo tissue).

By way of example only, the one or more physical sensors or devices 20 may be utilised to determine regions of tissue of a patient which have a different density, impedance, hardness, surface hardness, tissue hardness, tactile response, force response, radio-frequency absorbance, microwave reflectance or transmission, dielectric property, dielectric permittivity or conductivity, Young's modulus or capacitance or resistance compared to surrounding tissue. As will be appreciated, portions of tissue which have a different density, impedance, hardness, surface hardness, tissue hardness, tactile response, force response, radio-frequency absorbance, microwave reflectance or transmission, dielectric property, dielectric permittivity or conductivity, Young's modulus or capacitance or resistance compared to surrounding tissue may comprise diseased or potentially cancerous tissue. It is known, for example, that potentially cancerous tissue may be denser or harder than healthy tissue and may have a highly vascular nature. Accordingly, potentially cancerous tissue may have a different water content to that of surrounding healthy tissue, may have a higher or different temperature or surface hardness to that of healthy tissue and may have other different physical properties to that of surrounding healthy tissue.

According to an embodiment the additional or confirmatory information provided by the one or more physical sensors 20 may be used to help determine the margins or bounds of healthy, potentially cancerous, cancerous, potentially diseased or diseased biological tissue or the margins or bounds of a tumour.

The cancerous biological tissue or the tumour may comprise either: (i) grade I, grade II, grade III or grade IV cancerous tissue; (ii) metastatic cancerous tissue; (iii) mixed grade cancerous tissue; or (iv) a sub-grade cancerous tissue.

The one or more physical sensors 20 may be used to help determine physical or other non-mass spectrometric data and in particular may be used to determine the margins or bounds between different types or grades of diseased or cancerous tissue.

The different grades of cancerous tissue may be selected from the group consisting of: (i) grade I cancerous tissue; (ii) grade II cancerous tissue; (iii) grade III cancerous tissue; and (iv) grade IV cancerous tissue.

According to various embodiments a determination from the physical or other non-mass spectrometric data may be made to determine either: (i) one or more physical properties of the target; (ii) one or more chemical properties of the target; (iii) one or more physico-chemical properties of the target; or (iv) one or more mechanical properties of the target.

Optimised Operational Parameters of an Ambient Ionisation Surgical or Diagnostic Tool may be Programmed or Set Dependent upon Data Acquired from One or More Physical Sensors According to an embodiment one or more operational parameters of an ambient ionisation surgical or diagnostic tool may be arranged to vary or otherwise be optimised during a surgical or diagnostic procedure based upon the acquired physical or non-mass spectrometric data, chemical data, imaging data or other data.

For example, according to an embodiment the energy dissipated into surrounding tissue may be arranged to reduce as the surgical or diagnostic device approaches a vital organ.

According to various embodiments one more operational parameters of an ambient ionisation ion source may be varied or controlled depending upon the specific type of tissue which is being probed. The type of tissue may be known in advance or may be determined from imaging, chemical, physical or other data. For example, according to an embodiment if a tissue or tumour has a soft or gelatinous texture or the probe is in close proximity to a sensitive region of the body (e.g. the probe is in close proximity to important nerves) than the power and/or duty cycle of the ambient ionisation ion source may be reduced, varied or otherwise altered.

According to another embodiment, one or more operational parameters of an ambient ionisation surgical or other tool may be set based upon the acquired chemical data. For example, one or more operational parameters of an ambient ionisation surgical tool may be set based upon the type or grade of cancerous tissue identified by the one or more physical, chemical, imaging or other sensors or devices 20 or based upon the nature of the diseased tissue identified by the one or more physical, chemical, imaging or other sensors or devices 20.

Different operational parameters may be used depending upon whether operating upon healthy tissue, clearly cancerous tissue or at the cancer margin.

According to various embodiments the physical data, non-mass spectrometric data, chemical data, imaging data or other data may include spatial information and hence the variation of tissue as a function of depth within an organ may be determined. Accordingly, previously acquired physical data, non-mass spectrometric data, chemical data, imaging data or other data may be used to set various operational parameters of an ambient ionisation surgical tool as the surgical tool moves deeper into (or out of) an organ or closer to (or away from) an organ or specific tissue types.

Furthermore, various ionisation parameters may be varied as the ambient ionisation surgical tool moves deeper into (or out of) an organ or closer to (or away from) an organ or specific tissue types.

As the ambient ionisation surgical tool makes an initial cut into an organ one or more ionisation parameters (e.g. the composition of a matrix added to the aerosol, smoke or vapour released from the tissue, the temperature of a ionisation collision surface, the voltage applied to an ionisation collision surface etc.) may be optimised for the surgical conditions (e.g. initial blood loss, tissue composition) experienced when cutting into the organ. As the ambient ionisation surgical tool moves deeper into (or out of) the organ or closer to (or away from) an organ or specific tissue types the optimum ionisation parameters for the surgical tool may change reflecting e.g. a different degree of blood loss and a different composition of the tissue. Accordingly, one or more ionisation parameters (e.g. the composition of matrix added to aerosol, smoke or vapour released from the tissue, the temperature of a ionisation collision surface, the voltage applied to an ionisation collision surface etc.) may be arranged also to change or vary in order to match the changing surgical conditions and optionally based upon the acquired chemical data.

Numerous different embodiments are contemplated wherein various operational parameters of a surgical device or diagnostic tool which incorporates an ambient ionisation ion source (e.g. a rapid evaporative ionisation mass spectrometry ("REIMS") ion source) may be varied based upon the acquired physical non-mass spectrometric data, chemical data, imaging data or other data.

According to various embodiments an ion mode of the mass spectrometer and/or ion mobility spectrometer may be selected based upon chemical, physical, imaging or other data taken or determined from the cutting site.

According to further embodiments one or more operational parameters of the mass spectrometer and/or ion mobility spectrometer may be changed or altered based upon, subsequent to or during the process of making a diagnosis (e.g. of cancerous or healthy tissue). For example, one or more operational parameters may be changed upon confirmation. The one or more operational parameters which may be changed or optimised depending upon the stage of analysis (e.g. exploratory, diagnosis or confirmation) include optimisation of: (i) inlet conditions including inlet voltages, type and flow rate of optional matrix added to aerosol flow, Venturi suction etc.; (ii) fragmentation conditions for aerosol including flow rates and temperature of collision surface, heated coil parameters etc.; (iii) downstream ion optics including ion path; and (iv) mass analysis steps including selection of mass peak(s) for further diagnosis, performing MS/MS experiments, fragmenting analyte ions of interest and mass analysing subsequent daughter, fragment or product ions.

Combining Impedance Measurements of Tissue with Ambient Ionisation Analysis of Tissue According to various embodiments the one or more physical sensors 20 may comprise one or more impedance sensors which may be used to obtain the physical (or other related data) from a target (which may, for example, comprise in vivo or ex vivo tissue).

The one or more impedance sensors may be arranged to obtain the physical or other non-mass spectrometric data without the one or more impedance sensors physically contacting the target. Alternatively, the one or more impedance sensors may obtain the physical or other non-mass spectrometric data by physically contacting the target.

The data from the one or more impedance sensors may be used to determine a density, a density profile, an impedance or an impedance profile of one or more regions of the target.

According to an embodiment the physical or other non-mass spectrometric data which is obtained by the one or more impedance sensors may be used to determine one or more regions of interest. In particular, a determination may be made of one or more regions of the target which have a different density or impedance relative to normal tissue, surrounding tissue, a control sample, a control region, control data or predetermined data.

For example, a determination may be made as to whether or not a region of the target has a higher or lower density or impedance relative to normal tissue, surrounding tissue, a control sample, a control region, control data or predetermined data.

According to an embodiment the impedance sensor(s) may be used to acquire different dispersion impedance spectra. For example, according to various embodiments an impedance sensor may be used to acquire $\alpha$-dispersion impedance spectra (Hz to tens of kHz) which reflects the extracellular polarisation of cells. The impedance sensor may also be used to acquire $\beta$-dispersion impedance spectra (kHz to hundreds of MHz) which can be used to detect changes in the structural membrane of cells such as oedema or changes in the membrane thickness. The impedance sensor may also be used to acquire $\gamma$-dispersion impedance spectra (>hundreds of MHz) which reflects the relaxation of water and other small molecules.

For example, according to an embodiment impedance data may be measured at frequencies between 100 Hz and 10 MHz thus providing information on the $\alpha$- and $\beta$-dispersions of cells in either in vivo or ex vivo tissue.

Impedance data may be interpreted using a Cole-Cole approximation of the measurements in the complex impedance plane. Alternatively, the relative permittivity and conductivity for each measurement may be compared.

For example, a region of tissue of concern may be identified which has a greater or lesser impedance than that of surrounding healthy tissue.

According to an embodiment the step of using physical or other non-mass spectrometric data to determine one or more regions of interest may comprise the use of targeted nanoparticles containing or comprising a metal which is intended to change the electrical impedance of a targeted tissue type. As detailed below, metallic nanoparticles may be functionalised so that they adhere to specific types of tissue or other surfaces. One or more regions of interest of a target may be identified by determining one or more regions of a target (e.g., tissue) having a different impedance to other target areas due to the presence of targeted or functionalised nanoparticles which preferentially adhere to certain specific target areas (e.g., cancerous tissue).

In Vivo Impedance Measurements Made on Human Skin

Skin is the largest organ in the human body and is comprised of an inner hypodermis layer, an intermediate dermis layer and an outer epidermis layer. The outer epidermis layer provides a water impermeable barrier that prevents dehydration of the body. Fatty cells in the intermediate hypodermis act as insulation to prevent heat loss. The outer epidermis layer itself comprises different layers and the bottom layer of the epidermis, known as the stratum basale, contains melanin producing cells called melanocytes. Melanin gives the skin its colour and protects the nuclei of skin cell from ultra-violet damage. A mole or a benign naevus (N) comprises a cluster of melanocytes in the skin.

Skin cancers as a group are the most common form of human cancer and the Caucasian population is the most susceptible due to the low content of protective melanin.

Skin cancers may be broadly divided in two groups namely: (i) melanoma skin tumours e.g. malignant melanoma ("MM"); and (ii) non-melanoma skin tumours. Malignant melanomas account for the majority of deaths due to skin cancer and is a rapidly increasing type of malignant tumour.

Melanoma skin tumours may be sub-divided into: (i) superficial spreading melanoma ("SSM"); (ii) nodular malignant melanoma ("nodMM"); (iii) lentigo malignant melanoma ("LMM"); (iv) acral lentiginous melanoma; and (v) melanoma in situ ("Mis"). Non-melanoma skin tumours may be sub-divided into: (i) benign naevi ("N"); (ii) dysplastic naevi ("DN"); (iii) seborrhoic keratosis ("SK"); (iv) basal cell cancer ("BCC"); and (v) dermatofibroma ("DF").

Some types of skin tumour are benign including melanoma in situ ("Mis"), dysplastic naevus ("DN"), premalignant lentigo maligna ("LMM"), seborrheic keratosis ("SK") and dermatofibromas ("DF").

According to an embodiment an impedance sensor may be used to provide impedance or density data relating to the surface hardness of tissue.

According to Ohm's law impedance Z is the ratio between alternating voltage and alternating current. According to an embodiment a probe comprising two electrodes may be pressed against the surface of the skin and a small alternating voltage may be applied between the two electrodes. The resulting alternating current may then be measured. The voltage will be phase-shifted relative to the current due to the resistive and capacitive properties of the tissue. The impedance is given by:

$$Z=|Z|e^{i\Phi} \quad (1)$$

wherein Z is the impedance and $\Phi$ is the phase shift.

Surface Hardness or Tactile Sensors

It will be understood by those skilled in the art that the hardness of a tissue will be related to the composition of the tissue. Accordingly, if the composition of a tissue is altered by disease such as cancer then detecting a change in the surface hardness of the tissue can be a useful indicator of diseased tissue. Malignant tumours are often harder than the surrounding tissue and on this basis potential breast cancer can often be detected at an early stage during a routine physical examination. Similarly, prostate cancer can often be detected during a rectal examination.

Embodiments are disclosed wherein the one or more physical sensors 20 may comprise one or more sensors which are capable of determining the hardness of a tissue surface 2. Such embodiments are particularly beneficial since they enable the tissue 2 to be probed in a non-invasive manner.

According to an embodiment a rapid evaporative ionisation mass spectrometry ("REIMS") probe 1 may be provided with includes one or more tactile sensors based, for example, upon a vibrating piezoelectric device wherein the piezoelectric device may be arranged to contact the surface of the tissue 2. Contacting the surface of a tissue 2 will cause the resonance frequency of the piezoelectric device to change and the resulting frequency shift which is induced can then be detected. It will be understood that the frequency shift which is induced will be dependent upon the hardness of the underlying tissue 2.

According to an embodiment a rapid evaporative ionisation mass spectrometry ("REIMS") probe 1 may be provided comprising one or more strain gauge sensors. The strain gauge sensors may comprise semiconductor strain gauges and according to an embodiment four active strain gauges may be provided as a full Wheatstone bridge sensor. After calibration the output signal from the strain gauge bridge may be read as a force signal.

The one or more tactile sensors and the one or more strain gauge sensors may comprise separate sensor devices 20 as shown in FIG. 2 or alternatively the one or more sensors may be integrated into the rapid evaporative ionisation mass spectrometry ("REIMS") probe 1.

RF or Microwave Sensors

According to an embodiment one or more RF or microwave sensors may be used to obtain physical or other non-mass spectrometric data from one or more regions of a target.

Figure 3:
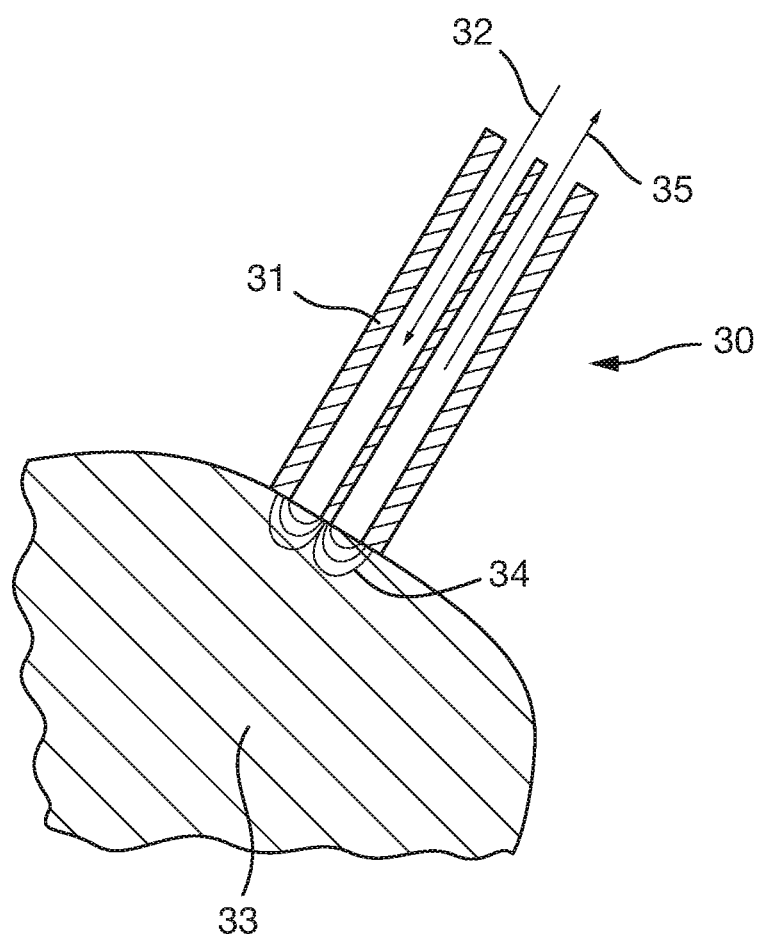
FIG. 3 shows a microwave reflectometry sensor which may be used according to various embodiments in order to obtain physical data.

FIG. 3 shows an RF or microwave sensor or device 30 which may be used to acquire physical data according to an embodiment. The RF or microwave sensor 30 may comprise a coaxial line probe 31 such that a microwave load 32 is directed into a target 33 which may comprise in vivo tissue such as lung or breast tissue. The microwave load 32 results in an electrical field 34 which penetrates a short distance into the target 33. A reflected signal 35 is captured by the coaxial line probe 31 and is detected by the RF or microwave sensor or device 30. One or more physical properties of the target or target tissue 33 may then be determined.

In particular, the RF sensor or device 30 may utilise microwaves at RF frequencies. In the case of breast tissue, normal breast tissue is substantially translucent to microwaves and there is a high dielectric contrast between malignant breast tumours and normal breast tissue. As a result, according to an embodiment a RF or microwave sensor 30 may be used to detect regions of e.g. breast tissue which are potentially cancerous. As a result, the physical data obtained by the RF or microwave sensor 30 may be used to direct a surgeon to specific areas of breast tissue which may then be subjected to a surgical procedure using an ambient ionisation ion source such as a rapid evaporative ionisation mass spectrometry ("REIMS") ion source. In particular, the physical data obtained by the RF or microwave sensor 30 may be used in conjunction with the ambient ionisation ion source to help determine the margins or bounds of potentially cancerous tissue with a high level of precision.

It will be appreciated that being able to determine to a high level of certainty that all undesired (e.g. potentially cancerous) tissue has been removed from a surgical site without also unnecessarily removing healthy tissue can have a significant positive impact upon potential surgical outcomes.

A pulsed confocal technique may be used together with time-gating in order to enhance the detection of tumours whilst suppressing the effects of tissue heterogeneity and absorption.

It is known to perform X-ray mammograms. However, there are concerns that repeated X-ray mammograms can result in an increased risk of cancer.

Therefore, one advantage of utilising RF or microwave technology according to various embodiments is that it avoids subjecting a patient to any increased risk (whether perceived or real) of cancer and also can be performed in a more relaxing and flexible environment which puts the patient at ease.

It is known that microwaves interact with biological tissue according to the water content of the tissue and that this interaction is quite different to the interaction of X-rays with biological tissue. In particular, using a microwave sensor or device 30 according to an embodiment can result in an order of magnitude improvement in terms of contrast compared to using either X-rays or ultrasound.

According to various embodiments the dielectric permittivity of a target which may comprise a specific type of tissue such as healthy in vivo breast or lung tissue may be determined in advance or may be determined during an initial procedure. The presence or absence of fluid (e.g., water) at the target or tissue 33 will impact upon the dielectric polarization. The microwave reflection coefficient will depend upon the dielectric properties of the target 33 and hence as a result the intensity of the reflected microwave signal will depend upon the fluid or water content of the tissue 33 which is being probed. As a result, the fluid or water content of the target or tissue 33 of interest can be determined and in particular areas of the target or tissue 33 which have a suspect fluid or water content can be identified.

In the case of lung tissue, for example, microwave reflectrometry measurements of the lung tissue enable the total tissue water content of the lung tissue to be determined. This can be useful in determining whether or not potentially cancerous lung tissue may be present. For example, healthy lung tissue may have a first water content (e.g., 77%) and cancerous lung tissue may have a second (higher) water content (e.g., 85%).

Furthermore, this approach can be useful in identifying the margins of a tumour in lung tissue. For example, the margins of the tumour may have a third (intermediate) water content (e.g., 82%) which is intermediate between the first water content of healthy tissue (77%) and the second water content of cancerous tissue (85%).

According to embodiments a microwave generator may be used to generate the microwave signal and the frequency of the signal emitted by the microwave generator may be varied from e.g. 5 MHz to e.g. 3 GHz as desired.

Embodiments are contemplated wherein the RF or microwave sensor 30 may be set to generate microwaves at a fixed frequency. Other embodiments are contemplated wherein the RF or microwave sensor or device 30 may be arranged to vary the frequency of microwaves which are output by the microwave sensor or device 30. For example, a target or tissue 33 may be probed by scanning the surface with a range of difference microwave frequencies and then determining the response or profile of the intensity of reflected microwaves as a function of the input frequency of the microwaves.

Malignant tumours may have significantly different dielectric constants to that of normal tissue and the high dielectric contrast may cause malignant tumours to have significantly greater microwave scattering cross sections compared to normal tissue.

According to an embodiment microwaves having a frequency in the range 4-10 GHz may be focused and pulsed into tissue 33 (e.g. human breast). Microwave energy will be backscattered upon encountering a tumour since the tumour has a significantly greater dielectric permittivity and conductivity compared to normal tissue. Backscattered energy may be collected or otherwise detected by a sensor or detector. A three dimensional image of the tumour can thus be constructed.

It is known that high water content tissue will have a different permittivity response as a function of frequency compared to low water content tissue.

The relative dielectric permittivity c and conductivity a of high water content tissue (such as muscle or malignant tumours) is about an order of magnitude higher than lower water content tissue (such as fat or normal breast tissue). This contrast between high and low water content tissue persists over a wide range of microwave frequencies and enables diseased tissue to be differentiated from healthy tissue.

Dielectric Property or Capacitive Sensors

Malignant tumours have significantly different dielectric constants to that of normal tissue and the large dielectric contrast causes malignant tumours to have significantly greater microwave scattering cross sections compared to normal tissue.

According to an embodiment a RF or microwave sensor may be provided wherein microwaves having a frequency in the range 4-10 GHz are optionally focused and optionally pulsed into in vivo tissue (e.g. human breast tissue). Microwave energy is backscattered upon encountering a tumour since the tumour has a significantly greater dielectric permittivity and conductivity compared to normal tissue. Backscattered energy may be collected by a sensor. A three dimensional image of the tumour may be constructed.

It is known that high water content tissue will have a different permittivity response as a function of frequency compared to low water content tissue.

The relative dielectric permittivity c and conductivity a of high water content tissue (such as muscle or malignant tumours) is about an order of magnitude higher than lower water content tissue (such as fat or normal breast tissue). This contrast between high and low water content tissue persists over a wide range of microwave frequencies.

It is known that connective tissue has a high water content and cancerous tissue has a relatively lower water content.

Accordingly, embodiments are contemplated wherein one or more dielectric property sensors or capacitive sensors are used to probe a target (e.g. in vivo tissue) and the resulting physical data is used to determine either directly or indirectly the water or fluid content of the target or tissue and hence to determine and identify regions of target or tissue which are potentially diseased, abnormal or otherwise cancerous.

Contrast Agents and Nanoparticles

The near-infrared ("NIR") may be used to interrogate tissues in combination with NIR excitable dyes or contrast agents.

Various embodiments are contemplated wherein endogenous or exogenous contrast agents may be used to enhance image data, physical data, chemical data or other data which may be acquired according to various embodiments.

A number of different contrast agents may be used to enhance image data, physical data, chemical data or other data which, for example, may fluorescence when illuminated with infrared radiation having a wavelength in the range 700-900 nm. The wavelength range 700-900 nm may be considered to comprise a therapeutic window since in vivo tissue exhibits a low absorbance in this wavelength range. Absorption occurs primarily from tissue chromophores of oxy- and deoxyhemoglobin, fat, melanin and water.

It will be understood that the ability to detect potentially abnormal or diseased tissue by imaging, chemical, physical or other techniques depends principally upon there being a contrast between healthy and diseased tissue.

Alternatively, abnormal or diseased tissue can be differentiated from healthy tissue on the basis of the two different tissue types having different scattering properties.

Although the wavelength range 700-900 nm is of particular interest due to the low absorbance in this wavelength range, infrared radiation in this wavelength range can also exhibit a relatively high scattering coefficient.

Embodiments are contemplated wherein imaging data, chemical data, physical data or other data may be obtained by detecting differences in the scattering of infrared radiation within the wavelength range 700-900 nm between healthy and diseased tissue.

Embodiments are also contemplated wherein one or more exogenous contrast agents may be used to analyse in vivo, ex vivo or in vitro tissue samples, biological matter, organic matter (including plastics), one or more bacterial colonies or one or more fungal colonies. According to an embodiment one or more exogenous fluorescence contrast agents may be provided or added to the tissue in order to augment endogenous contrast.

The one or more contrast agents may comprise one or more fluorescent contrast agents.

The one or more contrast agents may comprise one or more visible dyes.

The one or more contrast agents may comprise one or more radiocontrast agents.

The one or more contrast agents may comprise one or more optical, near infrared ("NIR"), fluorescent, autofluorescent or diagnostic contrast agents.

According to various embodiments the one or more contrast agents may be selected from the group consisting of: (i) indocyanine green ("ICG") and derivatives or conjugates of indocyanine green including indotricarbocyanine; (ii) diethylthiatricarbocyanine iodide ("DTTCI") and derivatives or conjugates of diethylthiatricarbocyanine iodide; (iii) rhodamine B and derivatives or conjugates of rhodamine B; (iv) photodynamic therapy ("PDT") agents including hexylpyropheophorbide ("HPPH"); (v) a cyanine dye including Cy 5.5 dyes; and (vi) bifunctional contrast agents. Indocyanine green ("ICG") is of particular interest since it has FDA approval for systemic administration. Indocyanine is excited at about 780 nm and emits at 830 nm. Indocyanine green will dissolve in blood and will bind to proteins such as albumin and lipoproteins. ICG is a nonspecific agent and is cleared rapidly from the blood. However, ICG tends to collect in regions of dense vascularity through extravascation. ICG may be administered to a patient at a dose of 0.2 mg/kg intravenously. Derivatives and conjugates of ICG may also be used.

Various embodiments are contemplated wherein ICG is excited using a 780 nm laser and fluorescent spectra at 830 nm are detected using a gain modulated image intensified charge coupled camera (ICCD).

Other embodiments are contemplated wherein magnetic nanoparticles ("MNPs") may be used as a contrast agent. The magnetic nanoparticles may comprise ferromagnetic iron oxide i.e. magnetite ($Fe_3O_4$) or maghemite ($\gamma$-$Fe_2O_3$) having a diameter in the range 1-100 nm. According to an embodiment the nanoparticles may have a diameter in the range 1-10, 10-20, 20-30, 30-40, 40-50, 50-60, 60-70, 70-80, 80-90 or 90-100 nm. In particular, various embodiments are contemplated wherein nanoparticles having a core diameter in the range of 5-15 nm may be used as contrast agents. In particular, as the size of the nanoparticles is reduced then the characteristics of the nanoparticles changes from having multi-domain ferromagnetic characteristics to having single domain characteristics and finally to having superparamagnetic characteristics. In particular, small nanoparticles having a diameter in the range 5-15 nm exhibit superparamagnetic properties having no hysteresis losses and will generate heat as a result of relaxational losses, mainly Neel relaxation loss. The inherent ferromagnetic properties of magnetic nanoparticles provides contrast enhancement with magnetic resonance ("MR") imaging. For example, accumulation of magnetic nanoparticles in brain tumours appears as a hypointensity on T2-weighted imaging including gradient echo imaging.

Magnetic nanoparticles may also be functionalised to target cancer cells thereby enabling cancerous tissue to be identified by magnetic resonance imaging.

According to an embodiment ultrasmall superparamagnetic iron oxide nanoparticles ("USPIONPs") may be used.

In addition to using nanoparticles to accumulate within cancerous tissue, according to further embodiments the nanoparticles may be heated by applying a magnetic field and in particular an alternating magnetic field ("AM F") which produces heat via relaxational loss via the Brownian Neel relaxation process or by hysteresis loss. As a result, potentially cancerous tissue can be identified on the basis of having an elevated or hyperthermic temperature relative to surrounding normal healthy tissue. Accordingly, thermal detection techniques in conjunction with the heating of nanoparticles which have accumulated in cancerous tissue may be used to visualise, image or target potentially cancerous tissue.

Further embodiments are contemplated wherein nanoparticles which have accumulated in cancerous tissue may be heated up to temperatures >40° C. in order to selectively target and kill cancerous cells. For example, heating cancerous cells to a temperature around 45° C. can cause cancer cells to undergo apoptosis or necrosis.

Furthermore, locally heating cancerous cells can increase the blood flow to the cancerous cells which can, for example, result in an improved delivery of chemotherapeutic agents to the cancerous cells. Also, cancer cells are more heat sensitive than normal tissue and so heat can be selectively applied to cancer cells in order to kill cancer cells without damaging surrounding normal or healthy tissue.

According to an embodiment the nanoparticles may comprise a polysiloxane matrix (Si) wherein chelating species such as diethylene triamine pentaacetic acid (DTPA) at the surface of the particles allows the complexation of metallic elements such as gadolinium (Gd), silicon (Si), calcium (Ca) and iron (Fe).

According to other embodiments the nanoparticles may be heated by radiofrequency capacitive heating wherein, for example, an alternating electrical current at 8 MHz may be applied and the temperature of tissues located between the electrodes increases. Magnetite cationic liposomes (MCLs) may be used and when injected into cancer cells the cancerous tissue may reach a temperature which is 2-3° C. above that of healthy tissue.

Other embodiments are contemplated wherein antibodies containing a ferromagnetic component may be used as a contrast agent.

The one or more contrast agents may be exogenous or endogenous to the target.

As is well known, fluorophores may be activated to an excited state by absorbing a photon and may then relax to a ground state in a non-radiative manner. Alternatively, the fluorophore may relax to the ground state in a radiative (fluorescence) manner. The fluorescence lifetime $\tau$ is equivalent to the mean time that a fluorophores remains in its activated state and the quantum efficiency is the proportion of relaxations which occur radiatively.

Other mechanisms are known wherein the excited state can undergo intersystem crossing to an intermediate excited state wherein the spin state of the electron is flipped and the relaxation of the intermediate excited state is forbidden until the electron spin is reversed. The lifetimes of the intermediate excited state may be of the order of microseconds to milliseconds and are termed phosphorescence.

Fluorescence radiative decay can be affected by pH, oxygenation, free ion concentrations, glucose and other analytes. Fluorescence can therefore provide an optical imaging ability which is not otherwise directly detectable.

According to an embodiment the fluorescence spectra of tissue may be analysed in order to determine the pH, oxygenation level or quantum efficiency of the tissue.

Other embodiments are contemplated wherein gamma ray imaging may be performed and optionally a technetium-99 sulfur colloid may be injected into the target tissue for analysis.

According to various embodiments gold nanoparticles ("Au NPs" or "GNPs") may be used as contrast agents. Gold nanoparticles may be formed by a laser ablation method wherein a gold target in water is subjected to pulsed laser irradiation. Colloidal gold can also be prepared by citrate reduction. Various other physical methods of producing gold nanoparticles are known including inert gas condensation, thermolysis of gold(I) complex, radiolysis of gold salts, photochemistry and sonochemistry. Chemical methods of producing gold nanoparticles are known including emulsification, reduction of gold ions in the presence of a dispersant, seed-mediated growth, use of reverse micelles and phase transfer reactions. Gold nanoparticles may also be biosynthesised by certain types of fungi including *Fusarium oxysporum, Verticillium* sp. and *Colletotrichum* sp. Gold nanoparticles have also been synthesized within HEK-293, HeLa, SiHa and SKNSH cells.

Gold nanoparticles may be readily functionalised generally through thiol linkages to provide functionalised gold nanoparticles (fGNPs) The surface of gold nanoparticles may be functionalised with e.g. cyclodextrin as a drug pocket having hydrophobic cavities, antibodies as a targeting moiety and poly(ethleneglycol) (PEG) as an anti-fouling shell. Anti-cancer drugs may be encapsulated into the hydrophobic cavity of the cyclodextrin and the gold nanoparticles may therefore be used as a drug delivery system (DDS).

According to various embodiments gold nanoparticles and in particular functionalised gold nanoparticles as described above may be used as contrast agents.

Gold nanoparticles cause local heating when irradiated with light (800-1200 nm) and hence gold nanoparticles may be used in the photothermal destruction of tumours according to various embodiments.

Plasmonic gold nanoparticles may be used for cancer diagnosis and photothermal therapy. Surface plasmon resonance ("SPR") leads to strong electromagnetic fields on the surface of gold nanoparticles which enhances all radiative properties such as absorption and scattering. In particular, Raman scattering is enhanced. Additionally, strongly absorbed light may be quickly converted to heat via a series of nonradiative processes.

Gold nanoparticles can be optically tuned by shape and structure and for example gold nanorods having different optical properties to gold nanospheres can be produced. The aspect ratio can be precisely controlled by changing experimental parameters in a seed-mediation growth method.

Gold nanoshells (comprising a silica core around 100 nm with a thin shell of gold a few nanometers thick) and gold nanocages may also be produced. Gold nanospheres, nanorods, nanostars and nanoshells may be used as contrast agents according to various embodiments.

According to an embodiment gold nanoparticles may be used for cancer imaging. It is known that gold nanoparticles scatter strongly and the scattering properties depend upon the size, shape and structure of the nanoparticles. According to an embodiment gold nanoparticles having a diameter 30-100 nm may be used. Such nanoparticles scatter intensely and can be detected using a microscope under dark field illumination conditions.

The gold nanoparticles may be conjugated with, for example, anti-epidermal growth factor receptors (anti-EGFR) antibodies (or other antibodies) to recognise the EGFR proteins (or other proteins) of cancer cells and tissues. The regular or well organised scattering pattern of nanoparticles bound to cancer cells can be readily distinguished from the random distribution of nanoparticles around healthy cells and this difference in scattering pattern may be utilised according to various embodiments.

The nanoparticles may be excited by white light from a halogen lamp.

According to an embodiment, functionalised gold nanoparticles may be distributed across the surface of a target (such as biological in vivo or ex vivo tissue) and the gold nanoparticles may preferentially bind to cancerous cells. As a result, cancerous regions of tissue can be identified by illuminating the target and either analysing the scattering pattern or measuring the scattered intensity of light.

For example, gold nanoparticles may have a strong surface plasmon resonance ("SPR") around 540 nm on the cell monolayer with the result that the nanoparticles scatter strongly in the green to yellow range of the visible spectrum. Similarly, gold nanorods may be constructed which exhibit a strong surface plasmon resonance ("SPR") around 800 nm giving an intense red colour.

Accordingly, gold nanoparticles may be used as imaging, physical or chemical contrast agents according to various embodiments.

Surface plasmon resonance ("SPR") effects also enhance the Raman scattering of adjacent molecules because the Raman intensity is directly proportional to the square of the field intensity imposed on the molecules. This phenomenon is termed as surface enhanced Raman scattering ("SERS").

According to an embodiment gold nanoparticles may be utilised in order to enhance Raman scattering of adjacent molecules. The gold nanoparticles may be either symmetric or asymmetric. According to an embodiment the gold nanoparticles may be asymmetric (e.g. nanorods) since asymmetric nanoparticles provide a larger Raman enhancement due to the lightening rod effect.

One particular advantage of using gold nanoparticles and surface enhance Raman scattering is that this approach greatly enhances detection sensitivity and decreases signal acquisition time.

According to another embodiment a Raman tag may be used as a spectroscopic imaging probe. The Raman tag may comprise organic dye molecules with aromatic structures which have relatively high Raman cross sections. Its fluorescence is quenched when they are adsorbed on to metallic nanoparticles and thus Raman signals are able to be detected.

The Raman tags may be physically adsorbed or chemically conjugated with both Raman tag and cancer targeting ligands.

According to other embodiments levan nanoparticles may be utilised for targeted cancer imaging. Levan is a biocompatible carbohydrate polymer that consists of β-D-fructofuranose attached by β-(2,6) linkages and is used in biomedical applications. According to an embodiment Indocyanine green (ICG) may be encapsulated in levan nanoparticles by self-assembly and the levan-ICG nanoparticles may be used for cancer imaging.

Various embodiments are contemplated wherein a target which may comprise biological tissue may be subjected to Raman or laser imaging (transmission or fluorescence) using nanoparticles such as gold nanoparticles are described above as contrast agents. One or more regions of interest may then be identified and the regions of interest may then be subjected to analysis using a first device to generate aerosol, smoke or vapour. The first device may comprise an ambient ionisation ion source such as a rapid evaporative ionisation mass spectrometry ("REIMS") ion source.

Other embodiments are contemplated wherein chemical tags (such as luminescent tags) may be used in combination with an ambient ionisation ion source such as a rapid evaporative ionisation mass spectrometry ("REIMS") ion source. For example, according to an embodiment a luminescent imaging, physical or chemical contrast agent may be modified with the inclusion of a ligand that is readily ionisable by an ambient ionisation ion source such as a rapid evaporative ionisation mass spectrometry ("REIMS") ion source. The contrast agents, tags or nanoparticles may be detected by mass spectrometry if an undesired (or desired) target or undesired (or desired) tissue is ablated. The tagging chemical may have fluorescent, magnetic, chemical, physical or other imaging properties and a part of the molecule may be arranged so as to ionise well for mass spectrometry analysis. For example, as described above, Indocyanine green (ICG) may be encapsulated into levan nanoparticles or more generally in functionalised nanoshells which are functionalised so as to target cancerous tissue or other undesired target material. Embodiments are contemplated wherein ICG (or other chemicals) which may be encapsulated within functionalised nanoparticles or nanoshells (which may be functionalised so as to target cancerous tissue) may be detected by mass spectrometry. Other embodiments are contemplated wherein one or more different markers other than ICG may be encapsulated into nanoparticles which target cancerous tissue. These one or more markers may then identified by mass spectrometry and a determination may be made that the tissue which is currently being analysed comprises cancerous tissue or otherwise comprises undesired target material.

Embodiments are contemplated wherein target experiments may be performed wherein a target is subjected to mass spectrometry analysis with a view to seeking to identify portions of target or tissue which include (or conversely do not include) a contrast agent, chemical tag, marker or nanoparticle wherein the contrast agent, chemical tag, marker or nanoparticle has been functionalised so as to target a particular target e.g. cancerous tissue. According to various embodiment identifying the presence of the contrast agent, chemical tag, marker or nanoparticle thereby enables a determination to be made that the target or tissue which is currently being analysed comprises cancerous tissue (or otherwise desired or undesired target material).

According to an embodiment the step of using physical or other non-mass spectrometric data to determine one or more regions of interest may comprise the use of targeted nanoparticles containing or comprising a metal which is intended to change the electrical impedance of a targeted tissue type. As detailed above, metallic nanoparticles may be functionalised so that they adhere to specific types of tissue or other surfaces. One or more regions of interest of a target may be identified by determining one or more regions of a target (e.g., tissue) having a different impedance to other target areas due to the presence of targeted or functionalised nanoparticles which preferentially adhere to certain specific target areas (e.g., cancerous tissue).

Photothermal Therapy (PTT)

Gold nanoparticles absorb light much more strongly than organic dye molecules. Nearly 100% adsorbed light is converted to heat via nonradiative properties. Accordingly, gold nanoparticles may be used as photothermal contrast agents for photothermal therapy wherein photon energy is converted to heat sufficient to induce cellular damage via thermal effects such as hyperthermia, coagulation and evaporation.

Photothermal therapy may be performed using spherical gold nanoparticles in conjunction with either pulsed or continuous wave lasers.

Nanosecond pulsed lasers may be used in conjunction with PTT to provide highly selective and localised damage to cancer cells without affecting neighbouring healthy cells which may be only a few nanometers to tens of micrometers away.

For in vivo therapy of tumours under the skin or deeply seated tumours within tissue near infrared (NIR) light may be used because of its deep penetration ability due to minimal absorption by hemoglobin and water molecules.

According to an embodiment PEGylated gold nanoshells may be used in conjunction with an ambient ionisation ion source since the absorption of gold nanoshells can be tuned to the NIR region. A continuous wave (cw) diode laser e.g. emitting at 820 nm with an irradiance of e.g. 35 W/cm$^2$ for 4 mins may be used to illuminate the gold nanoshells in order to cause cancer cell death of targeted cells.

The gold nanoshells may according to various embodiments be injected into the blood stream of a patient or spread upon the surface of a target or tissue sample.

Other embodiments are contemplated wherein PTT may be performed using gold nanorods. According to an embodiment a cw Ti:Sapphire laser emitting at 800 nm may be used in conjunction with gold nanorods.

According to an embodiment the target may be illuminated with either linearly polarized light or circularly polarized light. Illuminating gold nanorods with circularly polarized light is particularly beneficial as the light absorption by gold nanorods is enhanced leading to an ultra-low energy threshold for cancer killing.

It has been determined that a laser fluence of 30 J/cm$^2$ can result in an increase in temperature of the cells by about 10° C. which is sufficient to induce heat-stress cell death. Accordingly, a laser fluence of 30 J/cm$^2$ may be utilised according to various embodiments.

According to an embodiment gold nanorods may be conjugated to methoxy-poly (ethylene-glycol)-thiol having an average MW 5,000 (mPEG-SH-5000) and may be injected into a patient either intravenously and/or subcutaneously. Tumours or cancerous cells can be identified using transmission imaging of a NIR laser with a camera due to the NIR light absorption by the nanorods in the tumour.

Magnetic Resonance Elastography ("MRE")

Magnetic resonance elastography (MRE) is an experimental method of imaging propagating mechanical waves using MRI that can emulate palpation but with quantitative stiffness information for tissue characterization. MRE may be used in anatomic locations which are not manually accessible like the brain. It is accomplished by synchronising motion-sensitive phase contrast MRI sequences during the application of acoustic waves. The frequency of the acoustic waves is in the range of 100 Hz to 1 kHz. MRE creates images of propagating shear waves with variable wavelengths that are a function of the tissue shear modulus. The wavelength can be calculated by measuring the distances between black lines that show the waves in the MR image. The shear modulus and hence the stiffness of the tissue can be calculated to create a shear modulus map.

Ex vivo studies using hyperpolarized 3He, a noble gas used in lung studies, have demonstrated the feasibility of performing MRE in the lung. In this case it is the gas in the alveolar spaces and not the lung parenchyma that is used to measure the shear wave propagation.

Various embodiments are contemplated wherein magnetic resonance elastography may be utilised in order to determine one or more regions of interest in a target (e.g., biological tissue).

Further Ultrasound Methods

Transrectal ultrasound is used for the diagnosis and guiding of biopsy or prostate cancer as well as endoscopic ultrasound for lesion ID and also for biopsy. According to various embodiment rapid evaporative ionisation mass spectrometry ("REIMS") may be used as an intelligent biopsy device providing immediate feedback of results.

According to various embodiments capacitive micromachined ultrasonic transducer (CMUT) arrays may be utilised. The arrays may be provided on silicon substrates for non-invasive focused ultrasound ablation of lower abdominal cancers under MR guidance.

According to other embodiments endoscopic ultrasound guidance of brachytherapy may be performed using porous silicon microspheres containing phosphorus-32 introduced into the pancreas.

Acoustic Radiation Force Impulse Imaging

Acoustic radiation force impulse (ARFI) imaging has been shown to provide information about the mechanical properties of tissues. ARFI imaging may be used for the guiding of RF ablation of liver procedures.

Various embodiments are contemplated wherein acoustic radiation force impulse (ARFI) imaging may be utilised in order to determine one or more regions of interest in a target (e.g., biological tissue).

High Intensity Focused Ultrasound

Ultrasound elastography measures and displays tissue strain. Strain is the change in the dimension of tissue elements in different areas in a region of interest. Elastography uses ultrasound measurements made before and after a slight compression of tissue using a transducer. Sonoelastography is an in situ method that can be used to assess the mechanical properties of soft tissue qualitatively and quantitatively through ultrasonic ("US") imaging techniques.

Various embodiments are contemplated wherein ultrasound elastography may be utilised in order to determine one or more regions of interest in a target (e.g., biological tissue).

Photo and Thermo Acoustic Imaging

Thermo- and photo-acoustic imaging systems using hybrid imaging techniques may be used according to various embodiments which are able to combine the high contrast in microwave, RF and light absorption between healthy and tumour tissues with the high resolution of ultrasound. Due to increased haemoglobin and ionic water content tumour masses preferentially absorb more electromagnetic energy, heat and expand more quickly than nearby healthy tissue. These masses act as internal acoustic sources that create pressure waves. Ultrasound transducers surrounding the object may be used to detect the pressure waves.

Various embodiments are contemplated wherein thermo- and photo-acoustic imaging may be utilised in order to determine one or more regions of interest in a target (e.g., biological tissue).

Electrical Impedance Tomography

Electrical impedance tomography ("EIT") determines the electrical conductivity and permittivity distribution in the interior of a body from measurements made on its surface. Conducting electrodes are attached to the skin of the subject and small currents are applied to some or all of the electrodes and the corresponding electrical potentials are measured. EIT imaging in the body is based around measuring the impedance of tissues made up of cells, membranes and fluids. Various embodiments are contemplated wherein EIT may be utilised in order to determine regions of interest in a target (e.g. tissue) prior to analysis by an ambient ionisation ion source.

Cells and membranes have a high resistivity and act as small imperfect capacitors and contribute a frequency dependence. Fluids provide the resistive component of the impedance that has a frequency dependence only for liquids outside the cells.

High frequencies of the order a MHz show only the resistive component due to conduction through intracellular and extracellular fluids. Low frequencies in the range of a few Hz to several kHz cause the membranes to impede the flow of current and can be used to measure dimensions, shapes and electrical properties of cells.

Two types of imaging are possible: difference imaging and absolute imaging. Difference imaging is able to relate to changes in blood volume or cell size. Absolute imaging is more difficult as it needs to account for changes in electrode impedance and channel noise.

Prototype breast imagers have been developed that look for differences in bioimpedance that can differentiate malignant from benign lesions.

Analysing Sample Spectra

A list of analysis techniques which are intended to fall within the scope of the present invention are given in the following table:

| Analysis Techniques |
| --- |
| Univariate Analysis |
| Multivariate Analysis |
| Principal Component Analysis (PCA) |
| Linear Discriminant Analysis (LDA) |
| Maximum Margin Criteria (MMC) |
| Library Based Analysis |
| Soft Independent Modelling Of Class Analogy (SIMCA) |
| Factor Analysis (FA) |
| Recursive Partitioning (Decision Trees) |
| Random Forests |
| Independent Component Analysis (ICA) |
| Partial Least Squares Discriminant Analysis (PLS-DA) |
| Orthogonal (Partial Least Squares) Projections To Latent Structures (OPLS) |
| OPLS Discriminant Analysis (OPLS-DA) |
| Support Vector Machines (SVM) |
| (Artificial) Neural Networks |
| Multilayer Perceptron |
| Radial Basis Function (RBF) Networks |
| Bayesian Analysis |
| Cluster Analysis |
| Kernelized Methods |
| Subspace Discriminant Analysis |
| K-Nearest Neighbours (KNN) |
| Quadratic Discriminant Analysis (QDA) |
| Probabilistic Principal Component Analysis (PPCA) |
| Non negative matrix factorisation |
| K-means factorisation |
| Fuzzy c-means factorisation |
| Discriminant Analysis (DA) |

Combinations of the foregoing analysis approaches can also be used, such as PCA-LDA, PCA-MMC, PLS-LDA, etc.

Analysing the sample spectra can comprise unsupervised analysis for dimensionality reduction followed by supervised analysis for classification.

By way of example, a number of different analysis techniques will now be described in more detail.

Multivariate Analysis—Developing a Model for Classification

By way of example, a method of building a classification model using multivariate analysis of plural reference sample spectra will now be described.

Figure 4:
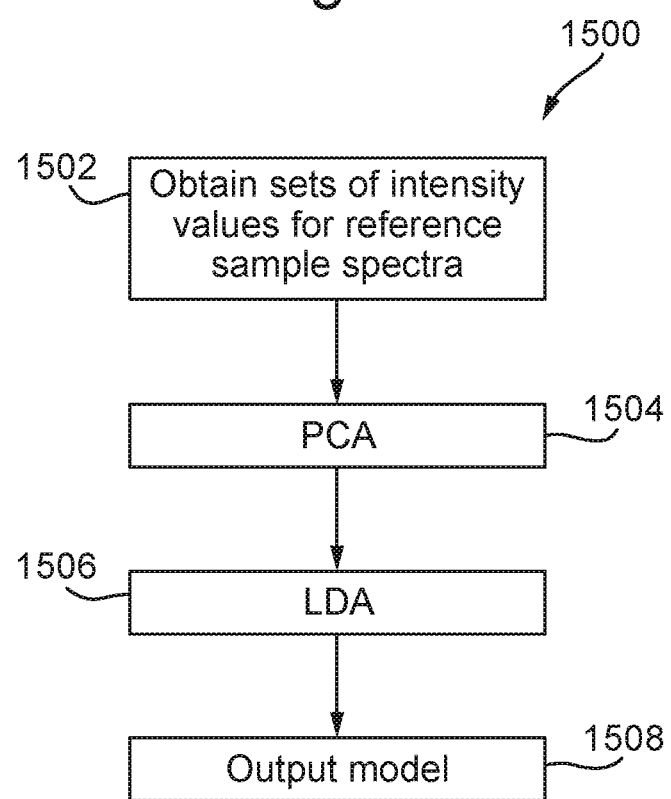
FIG. 4 shows a method of analysis that comprises building a classification model according to various embodiments.

FIG. 4 shows a method 1500 of building a classification model using multivariate analysis. In this example, the method comprises a step 1502 of obtaining plural sets of intensity values for reference sample spectra. The method then comprises a step 1504 of unsupervised principal component analysis (PCA) followed by a step 1506 of supervised linear discriminant analysis (LDA). This approach may be referred to herein as PCA-LDA. Other multivariate analysis approaches may be used, such as PCA-MMC. The PCA-LDA model is then output, for example to storage, in step 1508.

The multivariate analysis such as this can provide a classification model that allows an aerosol, smoke or vapour sample to be classified using one or more sample spectra obtained from the aerosol, smoke or vapour sample. The multivariate analysis will now be described in more detail with reference to a simple example.

Figure 5:
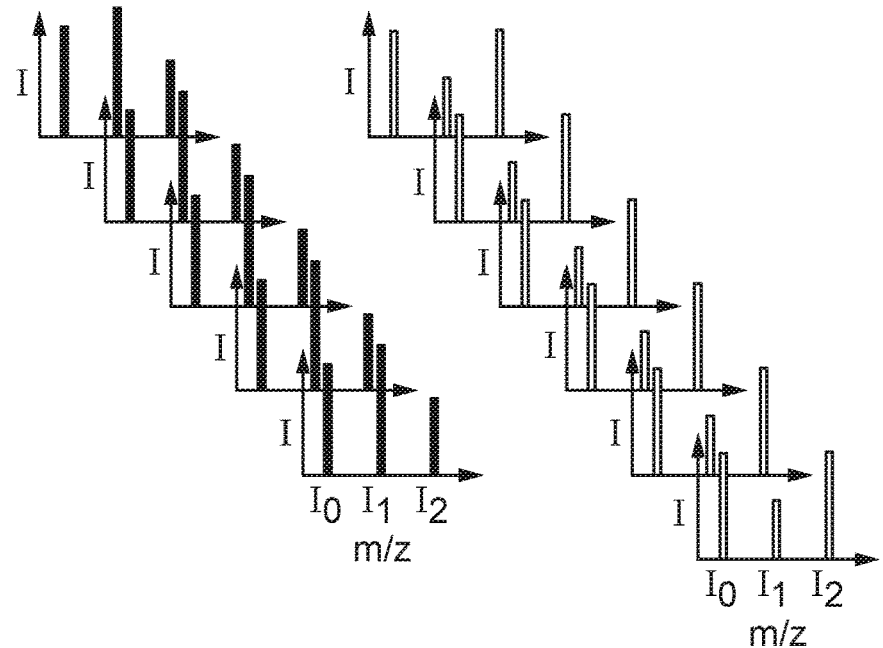
FIG. 5 shows a set of reference sample spectra obtained from two classes of known reference samples.

FIG. 5 shows a set of reference sample spectra obtained from two classes of known reference samples. The classes may be any one or more of the classes of target described herein. However, for simplicity, in this example the two classes will be referred as a left-hand class and a right-hand class.

Each of the reference sample spectra has been pre-processed in order to derive a set of three reference peak-intensity values for respective mass to charge ratios in that reference sample spectrum. Although only three reference peak-intensity values are hown, it will be appreciated that many more reference peak-intensity values (e.g., ~100 reference peak-intensity values) may be derived for a corresponding number of mass to charge ratios in each of the reference sample spectra. In other embodiments, the reference peak-intensity values may correspond to: masses; mass to charge ratios; ion mobilities (drift times); and/or operational parameters.

Figure 6:
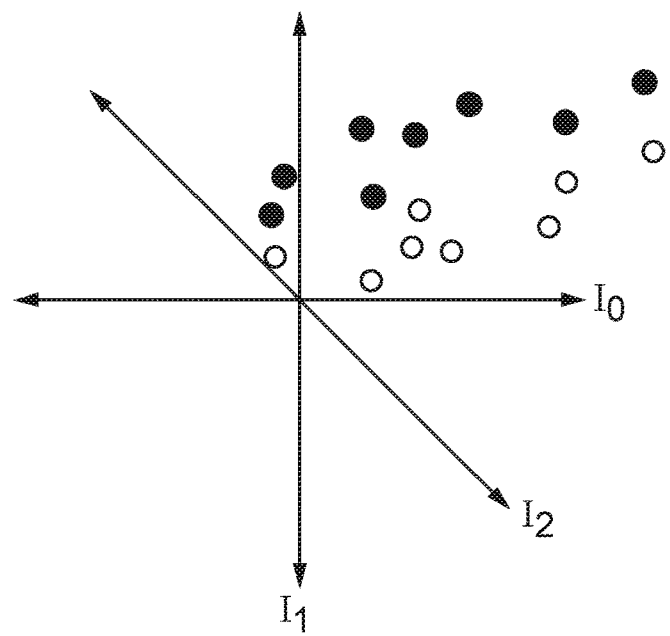
FIG. 6 shows a multivariate space having three dimensions defined by intensity axes, wherein the multivariate space comprises plural reference points, each reference point corresponding to a set of three peak intensity values derived from a reference sample spectrum.

FIG. 6 shows a multivariate space having three dimensions defined by intensity axes. Each of the dimensions or intensity axes corresponds to the peak-intensity at a particular mass to charge ratio. Again, it will be appreciated that there may be many more dimensions or intensity axes (e.g., ~100 dimensions or intensity axes) in the multivariate space. The multivariate space comprises plural reference points, with each reference point corresponding to a reference sample spectrum, i.e., the peak-intensity values of each reference sample spectrum provide the co-ordinates for the reference points in the multivariate space.

The set of reference sample spectra may be represented by a reference matrix D having rows associated with respective reference sample spectra, columns associated with respective mass to charge ratios, and the elements of the matrix being the peak-intensity values for the respective mass to charge ratios of the respective reference sample spectra.

In many cases, the large number of dimensions in the multivariate space and matrix D can make it difficult to group the reference sample spectra into classes. PCA may accordingly be carried out on the matrix D in order to calculate a PCA model that defines a PCA space having a reduced number of one or more dimensions defined by principal component axes. The principal components may be selected to be those that comprise or "explain" the largest variance in the matrix D and that cumulatively explain a threshold amount of the variance in the matrix D.

Figure 7:
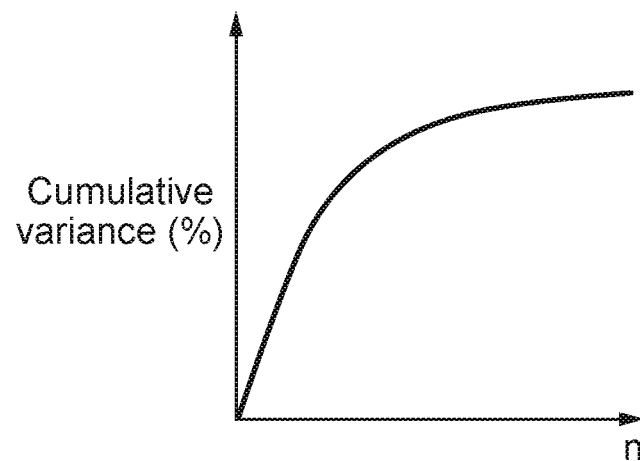
FIG. 7 shows a general relationship between cumulative variance and number of components of a PCA model.

FIG. 7 shows how the cumulative variance may increase as a function of the number n of principal components in the PCA model. The threshold amount of the variance may be selected as desired.

The PCA model may be calculated from the matrix D using a non-linear iterative partial least squares (NIPALS) algorithm or singular value decomposition, the details of which are known to the skilled person and so will not be described herein in detail. Other methods of calculating the PCA model may be used.

The resultant PCA model may be defined by a PCA scores matrix S and a PCA loadings matrix L. The PCA may also produce an error matrix E, which contains the variance not explained by the PCA model. The relationship between D, S, L and E may be:

$$D=SL^{\tau}+E \tag{2}$$

Figure 8:
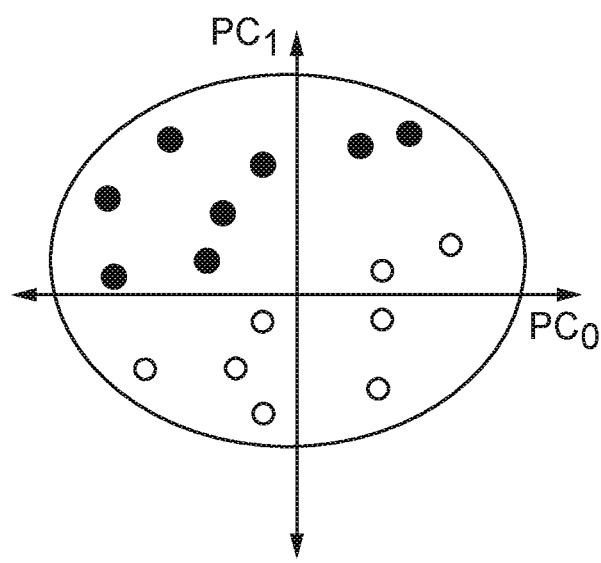
FIG. 8 shows a PCA space having two dimensions defined by principal component axes, wherein the PCA space comprises plural transformed reference points or scores, each transformed reference point or score corresponding to a reference point of FIG. 6.

FIG. 8 shows the resultant PCA space for the reference sample spectra of FIGS. 5 and 6. In this example, the PCA model has two principal components $PC_0$ and $PC_1$ and the PCA space therefore has two dimensions defined by two principal component axes. However, a lesser or greater number of principal components may be included in the PCA model as desired. It is generally desired that the number of principal components is at least one less than the number of dimensions in the multivariate space.

The PCA space comprises plural transformed reference points or PCA scores, with each transformed reference point or PCA score corresponding to a reference sample spectrum of FIG. 5 and therefore to a reference point of FIG. 6.

As is shown in FIG. 8, the reduced dimensionality of the PCA space makes it easier to group the reference sample spectra into the two classes. Any outliers may also be identified and removed from the classification model at this stage.

Further supervised multivariate analysis, such as multi-class LDA or maximum margin criteria (MMC), in the PCA space may then be performed so as to define classes and, optionally, further reduce the dimensionality.

As will be appreciated by the skilled person, multi-class LDA seeks to maximise the ratio of the variance between classes to the variance within classes (i.e., so as to give the largest possible distance between the most compact classes possible). The details of LDA are known to the skilled person and so will not be described herein in detail.

The resultant PCA-LDA model may be defined by a transformation matrix U, which may be derived from the PCA scores matrix S and class assignments for each of the transformed spectra contained therein by solving a generalised eigenvalue problem.

The transformation of the scores S from the original PCA space into the new LDA space may then be given by:

$$Z=SU \tag{3}$$

wherein the matrix Z contains the scores transformed into the LDA space.

Figure 9:
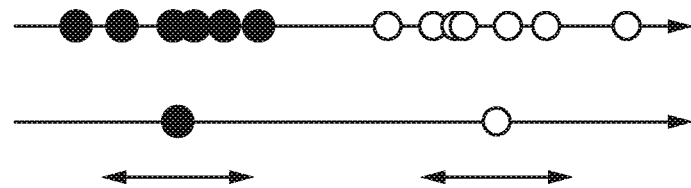
FIG. 9 shows a PCA-LDA space having a single dimension or axis, wherein the LDA is performed based on the PCA space of FIG. 8, the PCA-LDA space comprising plural further transformed reference points or class scores, each further transformed reference point or class score corresponding to a transformed reference point or score of FIG. 8.

FIG. 9 shows a PCA-LDA space having a single dimension or axis, wherein the LDA is performed in the PCA space of FIG. 8. As is shown in FIG. 9, the LDA space comprises plural further transformed reference points or PCA-LDA scores, with each further transformed reference point corresponding to a transformed reference point or PCA score of FIG. 8.

In this example, the further reduced dimensionality of the PCA-LDA space makes it even easier to group the reference sample spectra into the two classes. Each class in the PCA-LDA model may be defined by its transformed class average and covariance matrix or one or more hyperplanes (including points, lines, planes or higher order hyperplanes) or hypersurfaces or Voronoi cells in the PCA-LDA space.

The PCA loadings matrix L, the LDA matrix U and transformed class averages and covariance matrices or hyperplanes or hypersurfaces or Voronoi cells may be output to a database for later use in classifying an aerosol, smoke or vapour sample.

The transformed covariance matrix in the LDA space $V'_g$ for class g may be given by:

$$V'_g = U^\tau V_g U \quad (4)$$

wherein $V_g$ are the class covariance matrices in the PCA space.

The transformed class average position $z_g$ for class g may be given by:

$$s_g U = z_g \quad (5)$$

wherein $s_g$ is the class average position in the PCA space.

Multivariate Analysis—Using a Model for Classification

By way of example, a method of using a classification model to classify an aerosol, smoke or vapour sample will now be described.

Figure 10:
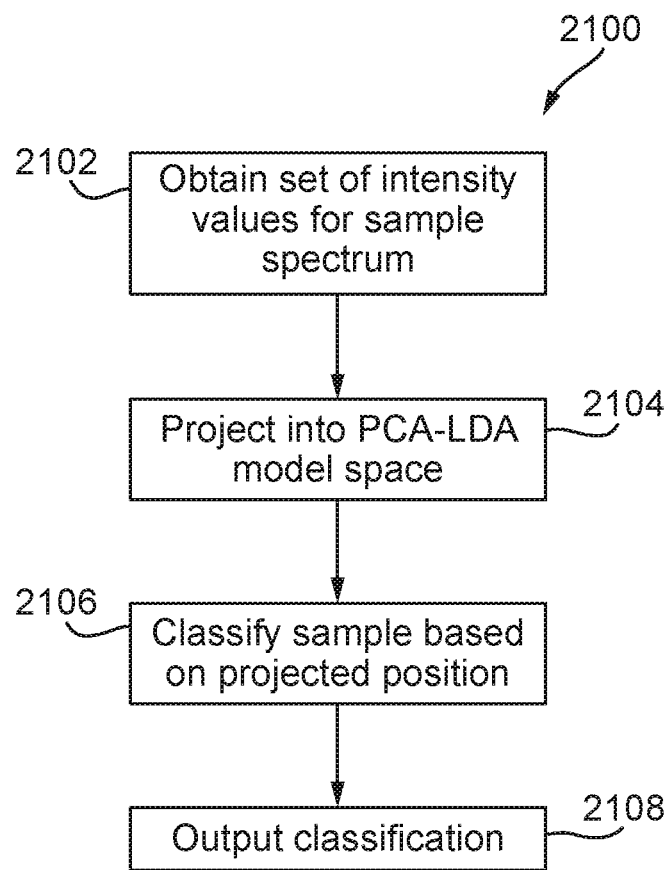
FIG. 10 shows a method of analysis that comprises using a classification model according to various embodiments.

FIG. 10 shows a method 2100 of using a classification model. In this example, the method comprises a step 2102 of obtaining a set of intensity values for a sample spectrum. The method then comprises a step 2104 of projecting the set of intensity values for the sample spectrum into PCA-LDA model space. Other classification model spaces may be used, such as PCA-MMC. The sample spectrum is then classified at step 2106 based on the project position and the classification is then output in step 2108.

Classification of an aerosol, smoke or vapour sample will now be described in more detail with reference to the simple PCA-LDA model described above.

Figure 11:
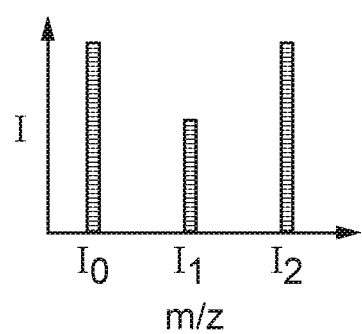
FIG. 11 shows a sample spectrum obtained from an unknown sample.

FIG. 11 shows a sample spectrum obtained from an unknown aerosol, smoke or vapour sample. The sample spectrum has been pre-processed in order to derive a set of three sample peak-intensity values for respective mass to charge ratios. As mentioned above, although only three sample peak-intensity values are shown, it will be appreciated that many more sample peak-intensity values (e.g., ~100 sample peak-intensity values) may be derived at many more corresponding mass to charge ratios for the sample spectrum. Also, as mentioned above, in other embodiments, the sample peak-intensity values may correspond to: masses; mass to charge ratios; ion mobilities (drift times); and/or operational parameters.

The sample spectrum may be represented by a sample vector $d_x$, with the elements of the vector being the peak-intensity values for the respective mass to charge ratios. A transformed PCA vector $s_x$ for the sample spectrum can be obtained as follows:

$$d_x L = s_x \quad (6)$$

Then, a transformed PCA-LDA vector $z_x$ for the sample spectrum can be obtained as follows:

$$s_x U = z_x \quad (7)$$

Figure 12:
FIG. 12 shows the PCA-LDA space of FIG. 9, wherein the PCA-LDA space further comprises a PCA-LDA projected sample point derived from the peak intensity values of the sample spectrum of FIG. 11.

FIG. 12 again shows the PCA-LDA space of FIG. 9. However, the PCA-LDA space of FIG. 12 further comprises the projected sample point, corresponding to the transformed PCA-LDA vector $z_x$, derived from the peak intensity values of the sample spectrum of FIG. 11.

In this example, the projected sample point is to one side of a hyperplane between the classes that relates to the right-hand class, and so the aerosol, smoke or vapour sample may be classified as belonging to the right-hand class.

Alternatively, the Mahalanobis distance from the class centres in the LDA space may be used, where the Mahalanobis distance of the point $z_x$ from the centre of class g may be given by the square root of:

$$(z_x - z_g)^\tau (V'_g)^{-1} (z_x - z_g) \quad (8)$$

and the data vector $d_x$ may be assigned to the class for which this distance is smallest.

In addition, treating each class as a multivariate Gaussian, a probability of membership of the data vector to each class may be calculated.

Library Based Analysis—Developing a Library for Classification

By way of example, a method of building a classification library using plural input reference sample spectra will now be described.

Figure 13:
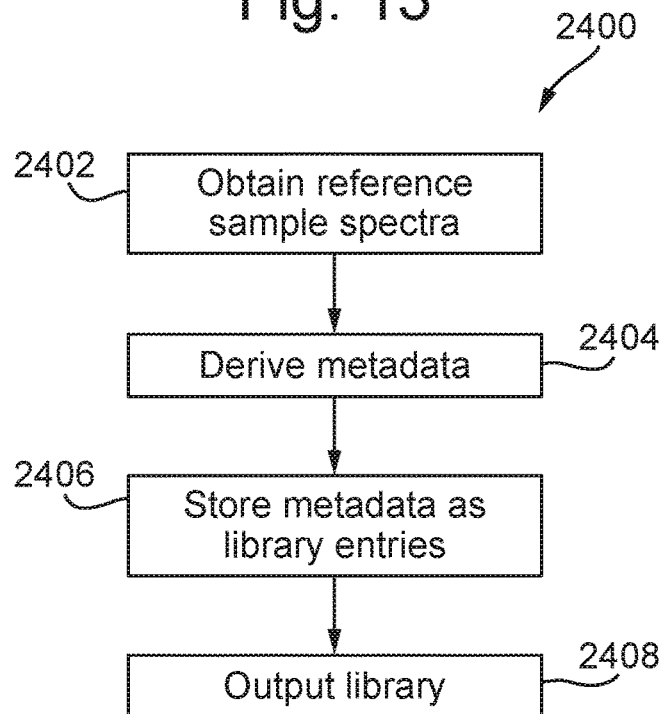
FIG. 13 shows a method of analysis that comprises building a classification library according to various embodiments.

FIG. 13 shows a method 2400 of building a classification library. In this example, the method comprises a step 2402 of obtaining plural input reference sample spectra and a step 2404 of deriving metadata from the plural input reference sample spectra for each class of sample. The method then comprises a step 2406 of storing the metadata for each class of sample as a separate library entry. The classification library is then output, for example to electronic storage, in step 2408.

A classification library such as this allows an aerosol, smoke or vapour sample to be classified using one or more sample spectra obtained from the aerosol, smoke or vapour sample. The library based analysis will now be described in more detail with reference to an example.

In this example, each entry in the classification library is created from plural pre-processed reference sample spectra that are representative of a class. In this example, the reference sample spectra for a class are pre-processed according to the following procedure:

First, a re-binning process is performed. In this embodiment, the data are resampled onto a logarithmic grid with abscissae:

$$x_i = \left\lfloor N_{chan} \log \frac{m}{M_{min}} \Big/ \log \frac{M_{max}}{M_{min}} \right\rfloor \quad (9)$$

wherein $N_{chan}$ is a selected value and denotes the nearest integer below x. In one example, $N_{chan}$ is $2^{12}$ or 4096.

Then, a background subtraction process is performed. In this embodiment, a cubic spline with k knots is then constructed such that p % of the data between each pair of knots lies below the curve. This curve is then subtracted from the data. In one example, k is 32. In one example, p is 5. A constant value corresponding to the q % quantile of the intensity subtracted data is then subtracted from each intensity. Positive and negative values are retained. In one example, q is 45.

Then, a normalisation process is performed. In this embodiment, the data are normalised to have mean $\bar{y}_i$. In one example, $\bar{y}_i = 1$.

An entry in the library then consists of metadata in the form of a median spectrum value $\mu_i$ and a deviation value $D_i$ for each of the $N_{chan}$ points in the spectrum.

The likelihood for the i'th channel is given by:

$$Pr(y_i \mid \mu_i, D_i) = \frac{1}{D_i} \frac{C^{C-1/2} \Gamma(C)}{\sqrt{\pi} \, \Gamma(C - 1/2)} \frac{1}{\left( C + \frac{(y_i - \mu_i)^2}{D_i^2} \right)^C} \quad (10)$$

where ½≤C<∞ and where Γ(C) is the gamma function.

The above equation is a generalised Cauchy distribution which reduces to a standard Cauchy distribution for C=1 and becomes a Gaussian (normal) distribution as C→∞. The parameter $D_i$ controls the width of the distribution (in the Gaussian limit $D_i=\sigma_i$ is simply the standard deviation) while the global value C controls the size of the tails.

In one example, C is 3/2, which lies between Cauchy and Gaussian, so that the likelihood becomes:

$$Pr(y_i | \mu_i, D_i) = \frac{3}{4} \frac{1}{D_i} \frac{1}{(3/2 + (y_i - \mu_i)^2 / D_i^2)^{3/2}} \quad (11)$$

For each library entry, the parameters $\mu_i$ are set to the median of the list of values in the i'th channel of the input reference sample spectra while the deviation $D_i$ is taken to be the interquartile range of these values divided by √2. This choice can ensure that the likelihood for the i'th channel has the same interquartile range as the input data, with the use of quantiles providing some protection against outlying data.

Library Based Analysis—Using a Library for Classification

By way of example, a method of using a classification library to classify an aerosol, smoke or vapour sample will now be described.

Figure 14:
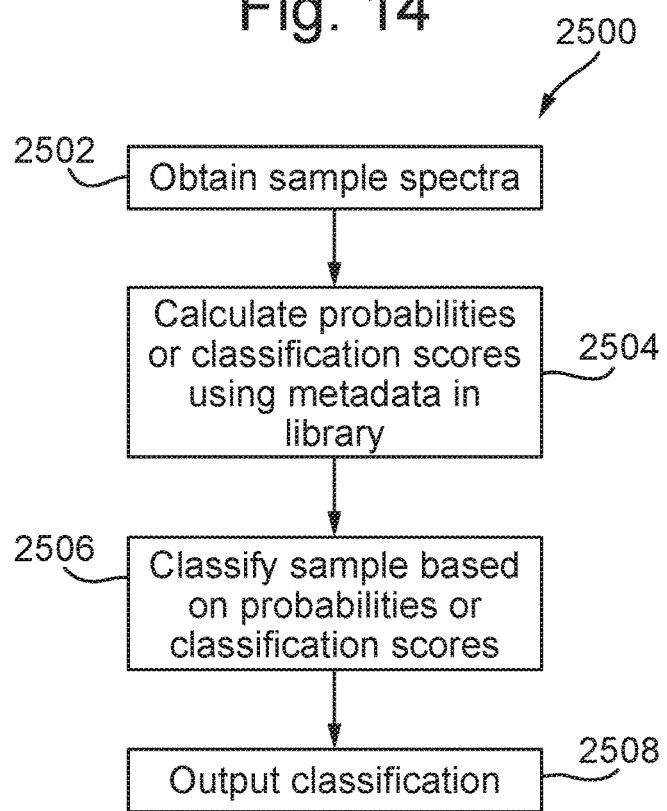
FIG. 14 shows a method of analysis that comprises using a classification library according to various embodiments.

FIG. 14 shows a method 2500 of using a classification library. In this example, the method comprises a step 2502 of obtaining a set of plural sample spectra. The method then comprises a step 2504 of calculating a probability or classification score for the set of plural sample spectra for each class of sample using metadata for the class entry in the classification library. The sample spectra are then classified at step 2506 and the classification is then output in step 2508.

Classification of an aerosol, smoke or vapour sample will now be described in more detail with reference to the classification library described above.

In this example, an unknown sample spectrum y is the median spectrum of a set of plural sample spectra. Taking the median spectrum y can protect against outlying data on a channel by channel basis.

The likelihood $L_s$ for the input data given the library entry s is then given by:

$$L_s = Pr(y | \mu, D) = \Pi_{i=1}^{Nchan} Pr(y_i | \mu_i, D_i) \quad (12)$$

wherein $\mu_i$ and $D_i$ are, respectively, the library median values and deviation values for channel i. The likelihoods $L_s$ may be calculated as log likelihoods for numerical safety.

The likelihoods $L_s$ are then normalised over all candidate classes 's' to give probabilities, assuming a uniform prior probability over the classes. The resulting probability for the class $\tilde{s}$ is given by:

$$Pr(\tilde{s} | y) = \frac{L_{\tilde{s}}^{(1/F)}}{\sum_s L_s^{(1/F)}} \quad (13)$$

The exponent (1/F) can soften the probabilities which may otherwise be too definitive. In one example, F=100. These probabilities may be expressed as percentages, e.g., in a user interface.

Alternatively, RMS classification scores $R_s$ may be calculated using the same median sample values and derivation values from the library:

$$R_s(y, \mu, D) = \sqrt{\frac{1}{N_{chan}} \sum_{i=1}^{N_{chan}} \frac{(y_i - \mu_i)^2}{D_i^2}} \quad (14)$$

Again, the scores $R_s$ are normalised over all candidate classes 's'.

The aerosol, smoke or vapour sample may then be classified as belonging to the class having the highest probability and/or highest RMS classification score.

Multivariate Analysis of Physical Data

Various further embodiments are contemplated wherein the physical data, chemical data, imaging data or other data may itself be subjected to multivariate analysis in order to assist, for example, in the identification of the target and/or to filter out outliers.

Methods of Medical Treatment, Surgery and Diagnosis and Non-Medical Methods

Various different embodiments are contemplated. According to some embodiments the methods disclosed above may be performed on in vivo, ex vivo or in vitro tissue. The tissue may comprise human or non-human animal tissue. Embodiments are contemplated wherein the target may comprise biological tissue, a bacterial or fungal colony or more generally an organic target such as a plastic).

Various embodiments are contemplated wherein analyte ions generated by an ambient ionisation ion source are then subjected either to: (i) mass analysis by a mass analyser such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly (or vice versa) ion mobility analysis (IMS) and/or differential ion mobility analysis (DMA) and/or Field Asymmetric Ion Mobility Spectrometry (FAIMS) analysis followed by secondly (or vice versa) mass analysis by a mass analyser such as a quadrupole mass analyser or a Time of Flight mass analyser. Various embodiments also relate to an ion mobility spectrometer and/or mass analyser and a method of ion mobility spectrometry and/or method of mass analysis. Ion mobility analysis may be performed prior to mass to charge ratio analysis or vice versa.

Various references are made in the present application to mass analysis, mass analysers, mass analysing, mass spectrometric data, mass spectrometers and other related terms referring to apparatus and methods for determining the mass or mass to charge of analyte ions. It should be understood that it is equally contemplated that the present invention may extend to ion mobility analysis, ion mobility analysers, ion mobility analysing, ion mobility data, ion mobility spectrometers, ion mobility separators and other related terms referring to apparatus and methods for determining the ion mobility, differential ion mobility, collision cross section or interaction cross section of analyte ions. Furthermore, it should also be understood that embodiments are contemplated wherein analyte ions may be subjected to a combination of both ion mobility analysis and mass analysis i.e. that both (a) the ion mobility, differential ion mobility, collision cross section or interaction cross section of analyte ions together with (b) the mass to charge of analyte ions is determined. Accordingly, hybrid ion mobility-mass spectrometry (IMS-MS) and mass spectrometry-ion mobility (MS-IMS) embodiments are contemplated wherein both the ion mobility and mass to charge ratio of analyte ions generated e.g. by an ambient ionisation ion source are determined. Ion mobility analysis may be performed prior to mass to charge ratio analysis or vice versa. Furthermore, it should be understood that embodiments are contemplated wherein references to mass spectrometric data and databases comprising mass spectrometric data should also be understood as encompassing ion mobility data and differential ion mobility data etc. and databases comprising ion mobility data and differential ion mobility data etc. (either in isolation or in combination with mass spectrometric data).

Various surgical, therapeutic, medical treatment and diagnostic methods are contemplated. However, other embodiments are contemplated which relate to non-surgical and non-therapeutic methods of mass spectrometry which are not performed on in vivo tissue. Other related embodiments are contemplated which are performed in an extracorporeal manner such that they are performed outside of the human or animal body.

Further embodiments are contemplated wherein the methods are performed on a non-living human or animal, for example, as part of an autopsy procedure.

Although the present invention has been described with reference to preferred embodiments, it will be understood by those skilled in the art that various changes in form and detail may be made without departing from the scope of the invention as set forth in the accompanying claims.

The invention claimed is:

1. A method comprising:
using one or more sensors to obtain or acquire physical non-mass spectrometric data from one or more regions of a target;
using said physical non-mass spectrometric data to determine one or more regions of interest of said target;
using a first device to generate aerosol, smoke or vapour from the one or more regions of interest of said target;
directing or aspirating at least some of said aerosol, smoke or vapour into a vacuum chamber of a mass spectrometer and/or ion mobility spectrometer;
causing said aerosol, smoke or vapour to impact upon a collision surface located within a vacuum chamber of said mass spectrometer and/or ion mobility spectrometer; and
mass analysing and/or ion mobility analysing said aerosol, smoke or vapour or ions derived from said aerosol, smoke or vapour in order to obtain mass spectrometric data and/or ion mobility data;
wherein said physical non-mass spectrometric data comprises data selected from the group consisting of: (i) density data; (ii) impedance data; (iii) hardness data; (iv) surface hardness data; (v) tissue hardness data; (vi) tactile data; (vii) radio-frequency absorbance data; (viii) microwave reflectance or transmission data; (ix) dielectric property data; (x) dielectric permittivity or conductivity data; (xi) Young's modulus data; and (xii) capacitance or resistance data.

2. The method as claimed in claim 1, wherein said target comprises native or unmodified target material, optionally wherein said native or unmodified target material is unmodified by the addition of a matrix or reagent.

3. The method as claimed in claim 1, further comprising mixing said aerosol, smoke or vapour with a matrix prior to, or as, said aerosol, smoke or vapour is directed or aspirated into said vacuum chamber of said mass spectrometer and/or ion mobility spectrometer.

4. The method as claimed in claim 1, further comprising changing, controlling, varying or optimising one or more operational parameters of said first device based upon said obtained physical non-mass spectrometric data.

5. The method as claimed in claim 1, further comprising using one or more contrast agents to enhance said physical non-mass spectrometric data.

6. An apparatus comprising:
one or more sensors arranged and adapted to obtain physical non-mass spectrometric data from one or more regions of a target;
a control system arranged and adapted to use said physical non-mass spectrometric data to determine one or more regions of interest of said target;
a first device arranged and adapted to generate aerosol, smoke or vapour from the one or more regions of interest of said target;
a mass analyser and/or ion mobility analyser for mass analysing and/or ion mobility analysing said aerosol, smoke or vapour or ions derived from said aerosol, smoke or vapour in order to obtain mass spectrometric data and/or ion mobility data;
a device for directing or aspirating at least some of said aerosol, smoke or vapour into a vacuum chamber of a mass spectrometer and/or ion mobility spectrometer; and
a device for directing said aerosol, smoke or vapour to impact upon a collision surface located within a vacuum chamber of said mass spectrometer and/or ion mobility spectrometer so as to generate a plurality of analyte ions;
wherein said physical non-mass spectrometric data comprises data selected from the group consisting of: (i) density data; (ii) impedance data; (iii) hardness data; (iv) surface hardness data; (v) tissue hardness data; (vi) tactile data; (vii) radio-frequency absorbance data; (viii) microwave reflectance or transmission data; (ix) dielectric property data; (x) dielectric permittivity or conductivity data; (xi) Young's modulus data; and (xii) capacitance or resistance data.

7. The apparatus as claimed in claim 6, further comprising a device for mixing said aerosol, smoke or vapour with a matrix prior to, or as, said aerosol, smoke or vapour is directed or aspirated into said vacuum chamber of said mass spectrometer and/or ion mobility spectrometer.

8. The apparatus as claimed in claim 6, wherein said first device comprises an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a focussed or unfocussed ultrasonic ablation device; (xxii) a microwave resonance device; and (xxiii) a pulsed plasma RF dissection device.

9. The apparatus as claimed in claim 6, wherein said first device is arranged and adapted to generate aerosol, smoke or vapour from one or more regions of said target by contacting said target with one or more electrodes.

10. The apparatus as claimed in claim 6, wherein said first device comprises a laser for irradiating said target.

11. The apparatus as claimed in claim 6, wherein said first device is arranged and adapted to direct ultrasonic energy into said target.

12. The apparatus as claimed in claim 6, wherein said physical non-mass spectrometric data obtained for said one or more target regions represents a value of a respective physical property at said one or more target regions, the apparatus further comprising a control system arranged and adapted to determine one or more regions of said target which have a different value of said physical property relative to normal tissue, surrounding tissue, a control sample, a control region, control data or predetermined data.

13. The apparatus as claimed in claim 6, further comprising a control system arranged and adapted to change, control, vary or optimise one or more operational parameters of said first device based upon said obtained physical or other non-mass spectrometric data.

14. A method as claimed in claim 3, wherein the matrix comprises isopropanol.

15. Apparatus as claimed in claim 6, wherein the one or more sensors comprise: (i) one or more impedance sensors for obtaining said physical non-mass spectrometric data; (ii) one or more force or tactile sensors for obtaining said physical non-mass spectrometric data; (iii) one or more radio-frequency ("RF") or microwave sensors for obtaining said physical non-mass spectrometric data; (iv) one or more dielectric property sensors or capacitive sensors for obtaining said physical non-mass spectrometric data; and/or (v) one or more electrochemical sensors or biosensors for obtaining said physical non-mass spectrometric data.

* * * * *

UNITED STATES PATENT AND TRADEMARK OFFICE
CERTIFICATE OF CORRECTION

PATENT NO. : 11,037,774 B2
APPLICATION NO. : 15/556052
DATED : June 15, 2021
INVENTOR(S) : Pringle et al.

Page 1 of 1

It is certified that error appears in the above-identified patent and that said Letters Patent is hereby corrected as shown below:

On the Title Page

Item (30) Foreign Application Priority Data, Page 2 -- Please replace "Sep. 9, 2015 (GB) .....151600" with "Sep. 9, 2015 (GB) .....1516003" --

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*